(12) United States Patent
LaVon et al.

(10) Patent No.: US 7,931,636 B2
(45) Date of Patent: Apr. 26, 2011

(54) SIMPLE DISPOSABLE ABSORBENT ARTICLE

(75) Inventors: Gary Dean LaVon, Liberty Township, OH (US); Richard Worthington Lodge, Colerain Township, OH (US); Kevin Michael Smith, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 91 days.

(21) Appl. No.: 11/197,197

(22) Filed: Aug. 4, 2005

(65) Prior Publication Data

US 2007/0032770 A1 Feb. 8, 2007

(51) Int. Cl.
*A61F 13/15* (2006.01)
*A61F 13/20* (2006.01)

(52) U.S. Cl. ........ 604/385.28; 604/385.201; 604/385.26

(58) Field of Classification Search .................. 604/386, 604/387, 385.04, 385.201, 385.26, 385.28
See application file for complete search history.

(56) References Cited

U.S. PATENT DOCUMENTS

| | | |
|---|---|---|
| 1,733,997 A | 10/1929 | Marr |
| 1,734,499 A | 11/1929 | Marinsky |
| 1,989,283 A | 1/1935 | Limacher |
| 2,058,509 A | 10/1936 | Rose |
| 2,271,676 A | 2/1942 | Bjornbak |
| 2,450,789 A | 10/1948 | Frieman |
| 2,508,811 A | 5/1950 | Best et al. |
| 2,568,910 A | 9/1951 | Condylis |
| 2,570,796 A | 10/1951 | Gross |
| 2,570,963 A | 10/1951 | Mesmer |
| 2,583,553 A | 1/1952 | Faure |
| 2,705,957 A | 4/1955 | Mauro |
| 2,788,786 A | 4/1957 | Dexter |
| 2,798,489 A | 7/1957 | Behrman |
| 2,807,263 A | 9/1957 | Newton |
| 2,830,589 A | 4/1958 | Doner |
| 2,890,700 A | 6/1959 | Lönberg-Holm |
| 2,890,701 A | 6/1959 | Weinman |
| 2,898,912 A | 8/1959 | Adams |

(Continued)

FOREIGN PATENT DOCUMENTS

EP 0 206 208 A1 12/1986

(Continued)

OTHER PUBLICATIONS

U.S. Appl. No. 11/133,818, filed May 20, 2005, LaVon et al.

(Continued)

*Primary Examiner* — Melanie J Hand
(74) *Attorney, Agent, or Firm* — Richard L. Alexander; Charles R. Ware

(57) ABSTRACT

A simple disposable pant-like garment includes a chassis and an absorbent assembly. The chassis, which can be extensible, includes a water-impermeable sheet folded laterally inward at both of its side edges to form opposing side flaps. Each side flap is attached to the interior surface of the chassis adjacent to its end edges. Each side flap has a longitudinally extending elastic gathering member attached adjacent to its proximal edge. The absorbent assembly is smaller in width and in length than the chassis. The side edges and end edges of the absorbent assembly can be disposed proximally relative to the respective side edges and end edges of the chassis. The absorbent assembly includes an absorbent core that can contain superabsorbent particles contained inside pockets. The absorbent assembly may be attached in a cruciform pattern to the chassis to allow portions of the chassis to extend laterally.

14 Claims, 23 Drawing Sheets

U.S. PATENT DOCUMENTS

| | | | |
|---|---|---|---|
| 2,931,361 A | 4/1960 | Sostsrin | |
| 2,977,957 A | 4/1961 | Clyne | |
| 3,207,158 A | 9/1965 | Yoshitake et al. | |
| 3,386,442 A | 6/1968 | Sabee | |
| 3,561,446 A | 2/1971 | Jones | |
| 3,572,342 A | 3/1971 | Lindquist et al. | |
| 3,578,155 A | 5/1971 | Small et al. | |
| 3,610,244 A | 10/1971 | Jones | |
| 3,618,608 A | 11/1971 | Brink | |
| 3,642,001 A | 2/1972 | Sabee | |
| 3,653,381 A | 4/1972 | Warnken | |
| 3,688,767 A | 9/1972 | Goldstein | |
| 3,710,797 A | 1/1973 | Marsan | |
| 3,731,688 A | 5/1973 | Litt et al. | |
| 3,756,878 A | 9/1973 | Willot | |
| 3,774,241 A | 11/1973 | Zerkle | |
| 3,776,233 A | 12/1973 | Schaar | |
| 3,814,100 A | 6/1974 | Nystrand et al. | |
| 3,828,784 A | 8/1974 | Zoephel | |
| 3,840,418 A | 10/1974 | Sabee | |
| 3,847,702 A | 11/1974 | Jones | |
| 3,848,595 A | 11/1974 | Endres | |
| 3,848,597 A | 11/1974 | Endres | |
| 3,860,003 A | 1/1975 | Buell | |
| 3,863,637 A | 2/1975 | MacDonald et al. | |
| 3,882,870 A | 5/1975 | Hathaway | |
| 3,884,234 A | 5/1975 | Taylor | |
| 3,900,032 A | 8/1975 | Heurlen | |
| 3,920,017 A | 11/1975 | Karami | |
| 3,924,626 A | 12/1975 | Lee et al. | |
| 3,926,189 A | 12/1975 | Taylor | |
| 3,929,134 A | 12/1975 | Karami | |
| 3,929,135 A | 12/1975 | Thompson | |
| 3,930,501 A | 1/1976 | Schaar | |
| 3,938,523 A | 2/1976 | Gilliland et al. | |
| 3,968,799 A | 7/1976 | Schrading | |
| 3,978,861 A | 9/1976 | Schaar | |
| 3,981,306 A | 9/1976 | Krusko | |
| 3,987,794 A | 10/1976 | Schaar | |
| 3,995,637 A | 12/1976 | Schaar | |
| 3,995,640 A | 12/1976 | Schaar | |
| 3,999,547 A | 12/1976 | Hernandez | |
| 4,014,338 A | 3/1977 | Schaar | |
| 4,034,760 A | 7/1977 | Amirsakis | |
| 4,074,508 A | 2/1978 | Reid | |
| 4,084,592 A | 4/1978 | Tritsch | |
| 4,100,922 A | 7/1978 | Hernandez | |
| 4,257,418 A | 3/1981 | Hessner | |
| 4,296,750 A | 10/1981 | Woon et al. | |
| 4,315,508 A | 2/1982 | Bolick | |
| 4,324,246 A | 4/1982 | Mullane et al. | |
| 4,342,314 A | 8/1982 | Radel et al. | |
| 4,388,075 A | 6/1983 | Mesek et al. | |
| 4,461,621 A | 7/1984 | Karami et al. | |
| 4,463,045 A | 7/1984 | Ahr et al. | |
| 4,475,912 A | 10/1984 | Coates | |
| 4,490,148 A | 12/1984 | Beckeström | |
| 4,585,450 A | 4/1986 | Rosch et al. | |
| 4,589,878 A | 5/1986 | Mitrani | |
| 4,601,717 A | 7/1986 | Blevins | |
| 4,610,678 A | 9/1986 | Weisman et al. | |
| 4,636,207 A | 1/1987 | Buell | |
| 4,670,011 A | 6/1987 | Mesek | |
| 4,680,030 A | 7/1987 | Coates et al. | |
| 4,681,581 A | 7/1987 | Coates | |
| 4,690,680 A | 9/1987 | Higgins | |
| 4,695,278 A | 9/1987 | Lawson | |
| 4,704,115 A | 11/1987 | Buell | |
| 4,704,116 A | 11/1987 | Enloe | |
| 4,731,066 A | 3/1988 | Korpman | |
| 4,747,846 A * | 5/1988 | Boland et al. | 604/385.22 |
| 4,781,711 A | 11/1988 | Houghton | |
| 4,784,892 A | 11/1988 | Storey | |
| 4,787,896 A | 11/1988 | Houghton et al. | |
| 4,795,454 A | 1/1989 | Dragoo | |
| 4,802,884 A | 2/1989 | Fröidh et al. | |
| 4,808,176 A | 2/1989 | Kielpikowski | |
| 4,834,735 A | 5/1989 | Alemany et al. | |
| 4,834,740 A | 5/1989 | Suzuki et al. | |
| 4,834,742 A | 5/1989 | Wilson et al. | |
| 4,838,886 A | 6/1989 | Kent | |
| 4,846,825 A | 7/1989 | Enloe et al. | |
| 4,861,652 A | 8/1989 | Lippert et al. | |
| 4,888,231 A | 12/1989 | Angstadt | |
| 4,892,528 A | 1/1990 | Suzuki et al. | |
| 4,892,536 A | 1/1990 | DesMarais et al. | |
| 4,904,251 A | 2/1990 | Igaue et al. | |
| 4,909,802 A | 3/1990 | Ahr et al. | |
| 4,909,803 A * | 3/1990 | Aziz et al. | 604/385.28 |
| 4,940,463 A | 7/1990 | Leathers et al. | |
| 4,940,464 A | 7/1990 | Van Gompel et al. | |
| 4,950,264 A | 8/1990 | Osborn | |
| 4,963,140 A | 10/1990 | Robertson et al. | |
| 4,968,313 A | 11/1990 | Sabee | |
| 4,990,147 A | 2/1991 | Freeland | |
| 5,006,394 A | 4/1991 | Baird | |
| 5,037,416 A | 8/1991 | Allen et al. | |
| 5,071,414 A | 12/1991 | Elliott | |
| 5,085,654 A * | 2/1992 | Buell | 604/370 |
| 5,092,861 A | 3/1992 | Nomura et al. | |
| 5,114,420 A | 5/1992 | Igaue et al. | |
| 5,135,522 A | 8/1992 | Fahrenkrug et al. | |
| D329,697 S | 9/1992 | Fahrenkrug et al. | |
| 5,151,092 A | 9/1992 | Buell et al. | |
| 5,190,606 A | 3/1993 | Merkatoris et al. | |
| 5,204,997 A | 4/1993 | Suzuki et al. | |
| 5,221,274 A | 6/1993 | Buell et al. | |
| 5,235,515 A | 8/1993 | Ungpiyakul et al. | |
| 5,246,431 A | 9/1993 | Minetola et al. | |
| 5,246,432 A | 9/1993 | Suzuki et al. | |
| 5,246,433 A | 9/1993 | Hasse et al. | |
| 5,260,345 A | 11/1993 | Desmarais et al. | |
| 5,269,775 A | 12/1993 | Freeland et al. | |
| 5,312,386 A | 5/1994 | Correa et al. | |
| 5,358,500 A | 10/1994 | LaVon et al. | |
| 5,366,782 A | 11/1994 | Curro et al. | |
| 5,387,209 A | 2/1995 | Yamamoto et al. | |
| 5,397,316 A | 3/1995 | Lavon et al. | |
| H1440 H | 5/1995 | New et al. | |
| 5,476,458 A | 12/1995 | Glaug et al. | |
| 5,518,801 A | 5/1996 | Chappell et al. | |
| 5,531,730 A | 7/1996 | Dreier | |
| 5,549,593 A | 8/1996 | Ygge et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,580,411 A | 12/1996 | Nease et al. | |
| 5,584,829 A | 12/1996 | Lavash et al. | |
| 5,607,416 A | 3/1997 | Yamamoto et al. | |
| 5,607,537 A | 3/1997 | Johnson et al. | |
| 5,607,760 A | 3/1997 | Roe | |
| 5,609,587 A | 3/1997 | Roe | |
| 5,622,589 A | 4/1997 | Johnson et al. | |
| 5,624,424 A | 4/1997 | Saisaka et al. | |
| 5,625,222 A | 4/1997 | Yoneda et al. | |
| 5,626,571 A | 5/1997 | Young et al. | |
| 5,635,191 A | 6/1997 | Roe et al. | |
| 5,643,588 A | 7/1997 | Roe et al. | |
| H1674 H | 8/1997 | Ames et al. | |
| 5,662,638 A | 9/1997 | Johnson et al. | |
| 5,674,215 A | 10/1997 | Ronnberg | |
| 5,691,035 A | 11/1997 | Chapell et al. | |
| 5,723,087 A | 3/1998 | Chappell et al. | |
| 5,749,866 A | 5/1998 | Roe et al. | |
| 5,752,947 A | 5/1998 | Awolin | |
| 5,772,825 A | 6/1998 | Schmitz | |
| 5,776,121 A | 7/1998 | Roe | |
| 5,779,831 A | 7/1998 | Schmitz | |
| 5,797,894 A | 8/1998 | Cadieux et al. | |
| 5,810,800 A | 9/1998 | Hunter et al. | |
| 5,814,035 A | 9/1998 | Gryskiewicz et al. | |
| 5,846,232 A | 12/1998 | Serbiak et al. | |
| 5,851,204 A | 12/1998 | Mizutani | |
| 5,865,823 A | 2/1999 | Curro | |
| 5,873,868 A | 2/1999 | Nakahata | |
| 5,876,391 A | 3/1999 | Roe et al. | |
| 5,891,544 A | 4/1999 | Chappell et al. | |

| | | | |
|---|---|---|---|
| 5,897,545 A | 4/1999 | Kline et al. | |
| 5,904,673 A | 5/1999 | Roe et al. | |
| 5,951,536 A | 9/1999 | Osborn, III et al. | |
| 5,957,908 A | 9/1999 | Kline et al. | |
| 5,968,029 A | 10/1999 | Chappell et al. | |
| 5,997,521 A | 12/1999 | Robles | |
| 6,004,306 A | 12/1999 | Robles et al. | |
| 6,022,430 A | 2/2000 | Blenke et al. | |
| 6,022,431 A | 2/2000 | Blenke et al. | |
| 6,042,673 A | 3/2000 | Johnson et al. | |
| 6,102,892 A | 8/2000 | Putzer et al. | |
| 6,107,537 A | 8/2000 | Elder et al. | |
| 6,110,157 A | 8/2000 | Schmidt | |
| 6,117,121 A | 9/2000 | Faulks et al. | |
| 6,120,486 A | 9/2000 | Toyoda et al. | |
| 6,120,487 A | 9/2000 | Ashton | |
| 6,120,489 A | 9/2000 | Johnson | |
| 6,120,866 A | 9/2000 | Arakawa et al. | |
| 6,129,720 A * | 10/2000 | Blenke et al. | 604/385.16 |
| 6,156,424 A | 12/2000 | Taylor | |
| 6,165,160 A | 12/2000 | Suzuki et al. | |
| 6,174,302 B1 | 1/2001 | Kumasaka | |
| 6,186,996 B1 | 2/2001 | Martin | |
| 6,210,390 B1 | 4/2001 | Karlsson | |
| 6,238,380 B1 | 5/2001 | Sasaki | |
| 6,241,716 B1 | 6/2001 | Rönnberg | |
| 6,322,552 B1 | 11/2001 | Blenke et al. | |
| 6,325,787 B1 | 12/2001 | Roe et al. | |
| 6,334,858 B1 | 1/2002 | Rönnberg et al. | |
| 6,350,332 B1 | 2/2002 | Thomas et al. | |
| 6,402,729 B1 | 6/2002 | Boberg et al. | |
| 6,402,731 B1 | 6/2002 | Suprise et al. | |
| 6,410,820 B1 | 6/2002 | McFall et al. | |
| 6,413,249 B1 | 7/2002 | Turi et al. | |
| 6,419,667 B1 | 7/2002 | Avalon et al. | |
| 6,432,098 B1 | 8/2002 | Kline et al. | |
| 6,432,099 B2 | 8/2002 | Rönnberg | |
| 6,443,933 B1 | 9/2002 | Suzuki et al. | |
| 6,461,342 B2 | 10/2002 | Tanji et al. | |
| 6,461,343 B1 | 10/2002 | Schaefer et al. | |
| 6,475,201 B2 | 11/2002 | Saito et al. | |
| 6,494,872 B1 | 12/2002 | Suzuki et al. | |
| 6,494,873 B2 | 12/2002 | Karlsson et al. | |
| 6,520,947 B1 | 2/2003 | Tilly et al. | |
| 6,524,294 B1 | 2/2003 | Hilston et al. | |
| 6,585,713 B1 | 7/2003 | LeMahieu et al. | |
| 6,602,234 B2 | 8/2003 | Klemp et al. | |
| 6,605,070 B2 | 8/2003 | Ludwig et al. | |
| 6,648,869 B1 | 11/2003 | Gillies et al. | |
| 6,648,870 B2 | 11/2003 | Itoh et al. | |
| 6,648,871 B2 | 11/2003 | Kusibojoska et al. | |
| 6,682,515 B1 | 1/2004 | Mizutani et al. | |
| 6,689,115 B1 | 2/2004 | Popp et al. | |
| 6,726,792 B1 | 4/2004 | Johnson et al. | |
| 6,755,808 B2 | 6/2004 | Balogh et al. | |
| 6,840,929 B2 | 1/2005 | Kurata | |
| 6,880,211 B2 | 4/2005 | Jackson et al. | |
| 6,923,797 B2 | 8/2005 | Shinohara et al. | |
| 6,962,578 B1 | 11/2005 | LaVon | |
| 6,972,010 B2 | 12/2005 | Pesce et al. | |
| 6,972,012 B1 * | 12/2005 | Pozniak et al. | 604/386 |
| 7,014,632 B2 | 3/2006 | Takino et al. | |
| 7,037,299 B2 | 5/2006 | Turi et al. | |
| 7,048,726 B2 | 5/2006 | Kusagawa et al. | |
| 7,160,281 B2 * | 1/2007 | LeMinh et al. | 604/385.22 |
| 2002/0045881 A1 | 4/2002 | Kusibojoska et al. | |
| 2002/0087139 A1 | 7/2002 | Popp et al. | |
| 2002/0123730 A1 * | 9/2002 | Popp et al. | 604/385.03 |
| 2002/0151861 A1 | 10/2002 | Klemp | |
| 2002/0173767 A1 | 11/2002 | Popp et al. | |
| 2003/0088223 A1 | 5/2003 | Vogt et al. | |
| 2003/0144644 A1 | 7/2003 | Murai et al. | |
| 2003/0148694 A1 | 8/2003 | Ghiam | |
| 2003/0233082 A1 | 12/2003 | Kline et al. | |
| 2004/0022998 A1 | 2/2004 | Miyamoto et al. | |
| 2004/0082928 A1 | 4/2004 | Pesce et al. | |
| 2004/0122411 A1 | 6/2004 | Hancock-Cooke | |
| 2004/0147890 A1 | 7/2004 | Nakahata et al. | |
| 2004/0162536 A1 | 8/2004 | Becker et al. | |
| 2004/0167486 A1 | 8/2004 | Busam et al. | |
| 2004/0225271 A1 | 11/2004 | Datta et al. | |
| 2004/0236299 A1 | 11/2004 | Tsang et al. | |
| 2004/0249355 A1 | 12/2004 | Tanio et al. | |
| 2005/0004543 A1 | 1/2005 | Schroer | |
| 2005/0004548 A1 | 1/2005 | Otsubo et al. | |
| 2005/0038401 A1 | 2/2005 | Suzuki et al. | |
| 2005/0085784 A1 * | 4/2005 | LeMinh et al. | 604/387 |
| 2005/0171499 A1 | 8/2005 | Nigam et al. | |
| 2005/0203475 A1 | 9/2005 | LaVon et al. | |
| 2005/0288645 A1 | 12/2005 | LaVon | |
| 2005/0288646 A1 | 12/2005 | LaVon | |
| 2006/0264860 A1 | 11/2006 | Beck | |

FOREIGN PATENT DOCUMENTS

| | | |
|---|---|---|
| EP | 403 832 | 12/1990 |
| EP | 0 761 194 A2 | 3/1997 |
| EP | 761194 A2 * | 3/1997 |
| EP | 0 893 115 A2 | 1/1999 |
| EP | 0 951 890 A2 | 1/1999 |
| EP | 916327 | 5/1999 |
| EP | 0 793 469 B1 | 6/2002 |
| EP | 1 224 922 A2 | 7/2002 |
| EP | 1 447 066 A1 | 8/2004 |
| EP | 1 447 067 A1 | 8/2004 |
| ES | 2 213 491 A1 | 8/2004 |
| FR | 2 566 631 A1 | 1/1986 |
| FR | 2 612 770 A1 | 9/1988 |
| FR | 2 810 234 A1 | 12/2001 |
| GB | 1 307 441 | 2/1973 |
| GB | 1 513 055 | 6/1978 |
| GB | 1513055 A * | 6/1978 |
| GB | 2 101 468 A | 1/1983 |
| GB | 2 262 873 A | 7/1993 |
| JP | 04 122256 A | 4/1992 |
| JP | 11318980 | 11/1999 |
| WO | WO 95/29657 A1 | 11/1995 |
| WO | WO 98/16179 A1 | 4/1998 |
| WO | WO 9913813 A * | 3/1999 |
| WO | WO 03/009794 A2 | 2/2003 |
| WO | WO 2004/105664 | 12/2004 |
| WO | WO 99/13813 A1 | 9/2005 |
| WO | WO 2005/087164 A1 | 9/2005 |
| WO | WO 2007/000315 A1 | 1/2007 |

OTHER PUBLICATIONS

U.S. Appl. No. 11/135,689, filed May 24, 2005, LaVon.
U.S. Appl. No. 11/140,888, filed May 31, 2005, LaVon et al.
U.S. Appl. No. 11/210,345, filed Aug. 24, 2005, LaVon et al.
U.S. Appl. No. 11/286,934, filed Nov. 23, 2005, LaVon et al.
International Search Report.

* cited by examiner

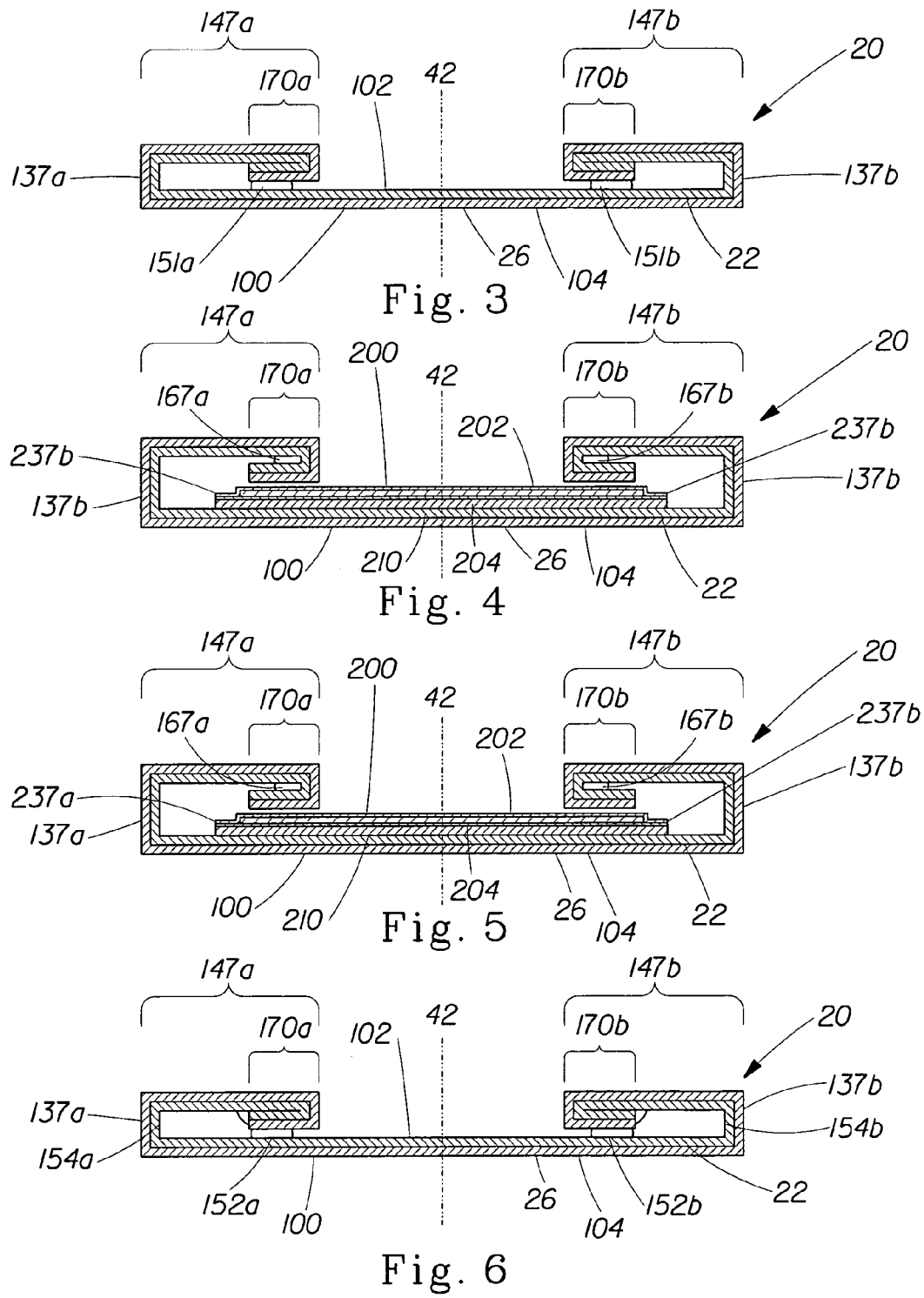

SIMPLE DISPOSABLE ABSORBENT ARTICLE

FIELD OF THE INVENTION

This invention relates to disposable absorbent articles such as disposable diapers and other articles intended for use on incontinent persons.

BACKGROUND OF THE INVENTION

Disposable absorbent articles are designed to absorb and contain bodily waste in order to prevent soiling of the body and clothing of the wearer, as well as bedding or other objects with which the wearer comes into contact. Pant-like garments, especially those of the "pull-on" type, include a pair of closed side interfaces that predefine encircled waist and leg openings. Accordingly, pull-on diapers can be more easily applied especially to a standing wearer than taped diapers, which require manual fastening to secure the diaper on the wearer.

As the usage of disposable absorbent articles has expanded, their complexity has increased with the incorporation of additional features serving to enhance their performance and appearance. The costs of the materials and the costs of the manufacturing processes have also increased in conjunction with the increase in complexity. As a result, the prices at which these articles are sold have risen to levels that many potential purchasers around the world cannot afford to pay. Thus, a need exists for a simple disposable absorbent article.

SUMMARY OF THE INVENTION

In accordance with one aspect of the invention, a disposable pant-like garment includes a chassis and an absorbent assembly. The chassis includes i. a front waist region; ii., a back waist region; iii. a crotch region between the waist regions; iv. laterally opposing first and second side edges defining its width; v. first and second side edge regions disposed adjacent, and including, the first and second side edges in the waist regions, wherein the first and second side edge regions include a pre-closed first and second interface, respectively; vi. longitudinally opposing front and back waist end edges defining its length; vii. an interior surface and an exterior surface; viii. a water-impermeable backsheet; and ix. laterally opposing side flaps attached to the interior surface adjacent to their longitudinally distal ends and each having a longitudinally extending elastic gathering member attached adjacent to its proximal edge. The absorbent assembly is attached to the chassis. At least a portion of the chassis underlying the absorbent assembly in one of the waist regions is laterally extensible.

In accordance with another aspect of the invention, a disposable pant-like garment includes a chassis and an absorbent assembly. The chassis includes a front waist region, a back waist region, and a crotch region between the waist regions, and first and second laterally opposing side edges defining its width, wherein the side edges are closed at respective first and second side interfaces. The chassis further has longitudinally opposing front and back waist end edges defining its length, an interior surface and an exterior surface, a water-impermeable backsheet, and laterally opposing side flaps attached to the interior surface adjacent to their longitudinally distal ends and each having a longitudinally extending elastic gathering member attached adjacent to its proximal edge. The absorbent assembly is attached to the interior surface of the chassis. At least a portion of the laterally opposing portions of the chassis located between the respective side edges of the chassis and the respective proximal edges of the side flaps are folded laterally inward to overlap the absorbent assembly and are attached to an interior surface of the absorbent assembly.

In accordance with still another aspect of the invention, a disposable pant-like garment includes a chassis having a front waist region, a back waist region, and a crotch region between the waist regions, laterally opposing side edges defining its width, longitudinally opposing front and back waist end edges defining its length, an interior surface and an exterior surface, a water-impermeable backsheet, and laterally opposing side flaps attached to the interior surface adjacent to their longitudinally distal ends and each having a longitudinally extending elastic gathering member attached adjacent to its proximal edge. The disposable pant-like garment further includes an absorbent assembly attached to the interior surface of the chassis. Laterally opposing portions of the chassis in at least the crotch region being folded laterally inward to form the side flaps, and laterally opposing portions of the chassis in at least one of the waist regions remaining unfolded so as to project laterally outward beyond the inward-folded portions and form laterally opposing side panels.

In accordance with yet another aspect of the invention, a disposable pant-like garment includes a chassis and an absorbent assembly. The chassis has a front waist region, a back waist region, and a crotch region between the waist regions, longitudinally opposing front and back waist end edges defining its length, laterally opposing side edges defining its width, and closed side edge regions disposed at the front and back waist regions. The absorbent assembly is attached to the chassis, such that a portion of the chassis disposed in an overlapping relationship with the absorbent assembly is laterally extensible.

BRIEF DESCRIPTION OF THE DRAWINGS

In the accompanying drawing figures, like reference numerals identify like elements, which may or may not be identical in the several exemplary embodiments that are depicted. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description.

FIG. 3 is a section view of the diaper illustrated in FIG. 1 taken along line 3-3;

FIG. 4 is a section view of the diaper illustrated in FIG. 1 taken along line 4-4;

FIG. 5 is a section view of the diaper illustrated in FIG. 1 taken along line 5-5;

FIG. 6 is a section view of the diaper illustrated in FIG. 1 taken along line 6-6;

DETAILED DESCRIPTION OF THE INVENTION

Definitions

Figure 1:
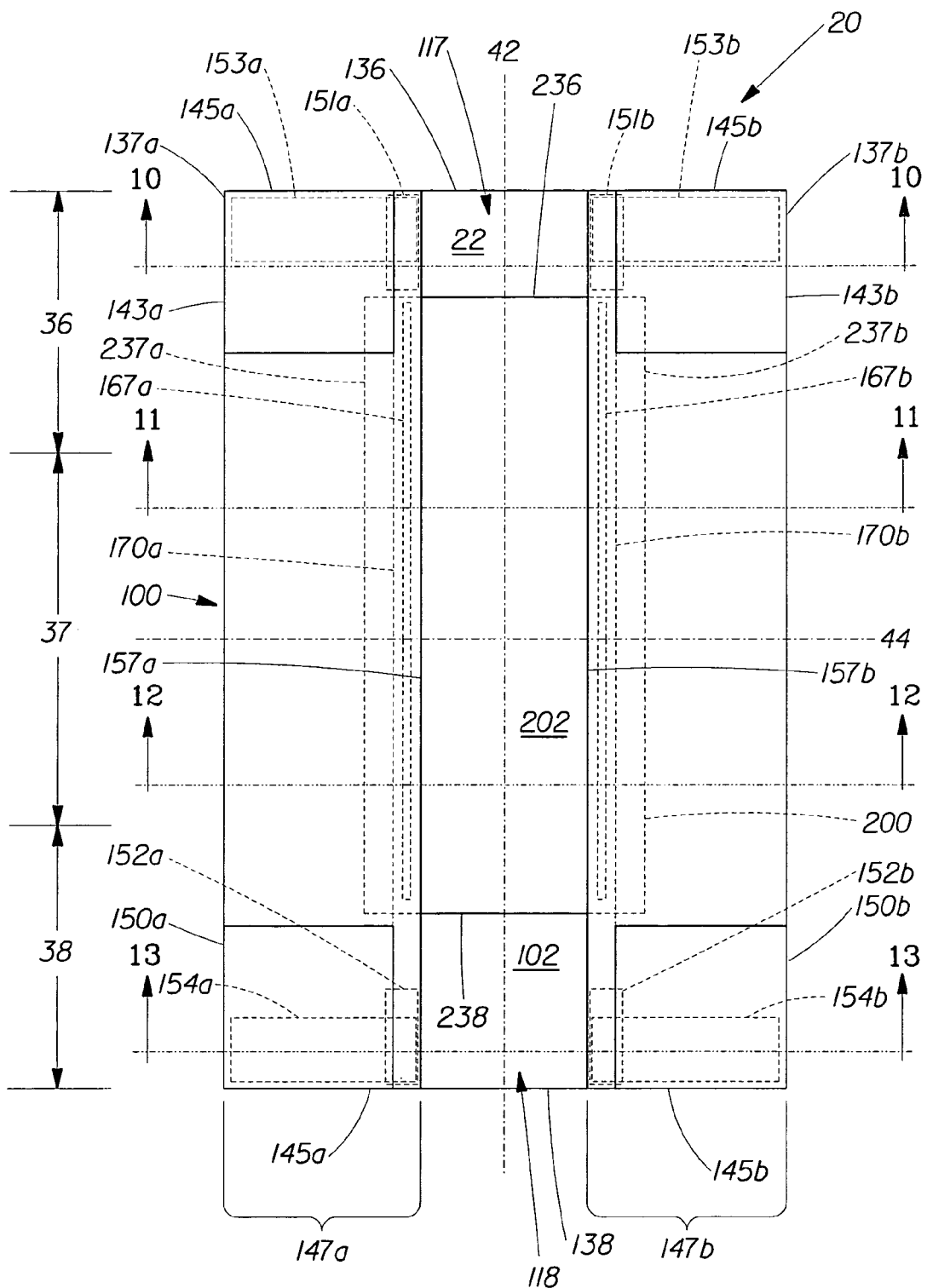
FIG. 1 is a plan view of a disposable absorbent article prior to being configured as a pull-on diaper, with the interior portion of the diaper that faces inwardly toward the wearer and contacts the wearer shown facing the viewer, in which the diaper is shown in its flat, uncontracted state (i.e., without the contraction induced by elastic members)

In this description, the following terms have the following meanings:

The term "absorbent article" refers to a device that absorbs and contains liquid and, more specifically, refers to a device that is placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

The term "diaper" refers to an absorbent article that is generally worn by infants and incontinent persons about the lower torso so as to encircle the waist and the legs of the wearer and that is specifically adapted to receive and contain urinary and fecal waste.

The term "closed side interface" refers to a given side edge (or region adjacent the side edge), wherein a portion of the side edge (or region adjacent the side edge) in the front waist region is joined to a portion of the same side edge (or region adjacent the side edge) in the rear waist region to define a closed, encircled leg openings and a closed waist opening. The side interface can be closed with a refastenable or permanent closure member.

The term "pant" (also referred to as "training pant", "closed diaper", and "pull-on diaper") refers to disposable garments having a continuous perimeter waist opening and continuous perimeter leg openings designed for infant or adult wearers. A pant can be configured with a continuous or closed waist opening and at least one continuous, closed, leg opening prior to the article being applied the wearer for use. A pant can be preformed by any suitable technique including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened, front waist fastened, rear waist fastened). Examples of suitable pants are disclosed in U.S. Pat. Nos. 5,246,433; 5,569,234; 6,120,487; 6,120,489; 4,940, 464; 5,092,861; 5,897,545; 5,957,908; and U.S. Patent Publication No. 2003/0233082 A1.

The term "closure member" refers to an element that maintains the article waist and leg openings in a closed, continuous, configuration until the closure member is released. Suitable closure members include a seam, an adhesive, a cohesive, a heat bond, a pressure bond or weld, a tab-and-slot configuration, a hook-and-loop configuration, and the like.

The term "refastenable closure member" refers to a closure member that can be opened and subsequently re-closed, reliably, without destroying the closure member or surrounding diaper components. Examples of refastenable closure members include seams, tabs-and-slots, hooks-and-loops, peelable adhesives, cohesives, and the like The term "permanent closure member" refers to a closure member that cannot be opened without causing the closure member to fail (i.e., the closure member cannot again be reliably closed). At times, when attempting to open a permanent closure member, surrounding absorbent article component(s) may be damaged or torn. Examples of permanent closure members include adhesives, cohesives, and the like, and further include seams.

The term "seam" refers to an elongated line of junction that attaches two regions of a diaper chassis. Seams can be created thermal bonds, pressure bonds, ultrasonic bonds, adhesive bonds, welds, and stitching A seam can be configured as a permanent or refastenable closure member.

The term "cohesive" refers to the property of a material that sticks to itself but does not to any significant degree stick to other materials.

The term "disposable" refers to the nature of absorbent articles that generally are not intended to be laundered or otherwise restored or reused as an absorbent article, i.e., they are intended to be discarded after a single use and, preferably, to be recycled, composted or otherwise disposed of in an environmentally compatible manner.

The term "extensible" refers to any material which, upon application of a biasing force of less than 500 grams/inch is elongatable, at least about 20 percent without experiencing catastrophic failure.

The term "longitudinal" refers to a direction running from a waist edge to an opposing waist edge of the article and generally parallel to the maximum linear dimension of the article. Directions within ±45° of the longitudinal direction are considered to be "longitudinal".

The term "lateral" refers to a direction running from a side edge to an opposing side edge of the article and generally at a right angle to the longitudinal direction. Directions within ±45° of the lateral direction are considered to be "lateral".

The term "disposed" refers to an element or region being attached and/or positioned in a particular place or position in a unitary structure with other elements.

The term "attached" refers to elements being connected or united by fastening, adhering, bonding, etc. by any method suitable for the elements being attached together and their constituent materials. Many suitable methods for attaching elements together are well-known, including adhesive bonding, pressure bonding, thermal bonding, mechanical fastening, etc. Such attachment methods can be used to attach elements together over a particular area either continuously or intermittently.

The terms "water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water to pass through its thickness in the absence of a forcing pressure. Conversely, the term "water-impermeable" refers to a layer or a layered structure through the thickness of which liquid water cannot pass in the absence of a forcing pressure. A layer or a layered structure that is water-impermeable according to this definition can be permeable to water vapor, i.e., can be "vapor-permeable". As is well known in the art, a common method for measuring the permeability to water of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables And Nonwovens Association).

The terms "proximal" and "distal" refer respectively to the location of an element near to or far from the center of a structure, e.g., the proximal edge of a longitudinally extending element is located nearer to the longitudinal axis than the distal edge of the same element is located relative to the same longitudinal axis.

Description of Exemplary Diaper Embodiment

As shown in FIGS. 1-6, one end portion of an absorbent article, illustrated as an exemplary pant-like garment, also referred to as a pant or a pull-on diaper 20, is configured as a front waist region 36. The longitudinally opposing end portion of the pull-on diaper 20 is configured as a back waist region 38. An intermediate portion of the pull-on diaper 20 extending longitudinally between the front waist region 36 and the back waist region 38 is configured as a crotch region 37.

The basic structure of the pull-on diaper 20 includes a chassis 100 having a laterally extending front waist edge 136 in the front waist region 36 and a longitudinally opposing and laterally extending back waist edge 138 in the back waist region 38. The chassis 100 has a longitudinally extending left side edge 137a and a laterally opposing and longitudinally extending right side edge 137b, both chassis side edges extending longitudinally between the front waist edge 136 and the back waist edge 138. The chassis 100 has an interior surface 102 and an exterior surface 104. The chassis 100 also has a longitudinal axis 42 and a lateral axis 44. The longitudinal axis 42 extends through the midpoint of the front waist edge 136 and through the midpoint of the back waist edge 138 of the chassis 100. The lateral axis 44 extends through the midpoint of the left side edge 137a and through the midpoint of the right side edge 137b of the chassis 100. The exemplary chassis 100 shown in FIG. 1 additionally has longitudinally extending and laterally opposing side flaps 147a and 147b that are described in more detail below.

The basic structure of the pull-on diaper 20 also includes an absorbent assembly 200 that is attached to the chassis 100. The absorbent assembly 200 has a laterally extending front edge 236 in the front waist region 36 and a longitudinally opposing and laterally extending back edge 238 in the back waist region 38. The absorbent assembly 200 has a longitudinally extending left side edge 237a and a laterally opposing and longitudinally extending right side edge 237b, both absorbent assembly side edges extending longitudinally between the front edge 236 and the back edge 238. The absorbent assembly 200 has an interior surface 202 and an exterior surface 204. The absorbent assembly 200 can be disposed symmetrically with respect to either or both of the longitudinal axis 42 and the lateral axis 44. Alternatively, the absorbent assembly 200 can be disposed asymmetrically with respect to either or both of the longitudinal axis 42 and the lateral axis 44. For example, the absorbent assembly 200 shown in FIG. 1 is disposed symmetrically with respect to the longitudinal axis 42 and asymmetrically with respect to the lateral axis 44. In particular, the absorbent assembly 200 shown in FIG. 1 is disposed asymmetrically toward the front waist region 36.

The respective front edge 236, back edge 238, left side edge 237a, and right side edge 237b of the absorbent assembly 200 can lie inward of the respective front waist edge 136, back waist edge 138, left side edge 137a, and right side edge 137b of the chassis 100, as in the exemplary pull-on diaper 20 shown in FIG. 1. Such a configuration in which one or more of the edges of the absorbent assembly 200 lies inward of the corresponding edges of the chassis 100 may be desirable, for example, in order to allow the relatively more flexible layer or layers adjacent to the edges of the chassis to conform to the body of the wearer and thereby form effective gasket-like seals against the skin of the wearer without being constrained by a relatively thicker and relatively less flexible absorbent assembly. Alternatively, one or more of the edges of the absorbent assembly 200 can coincide with the corresponding edge or edges of the chassis 100.

Figure 8A:
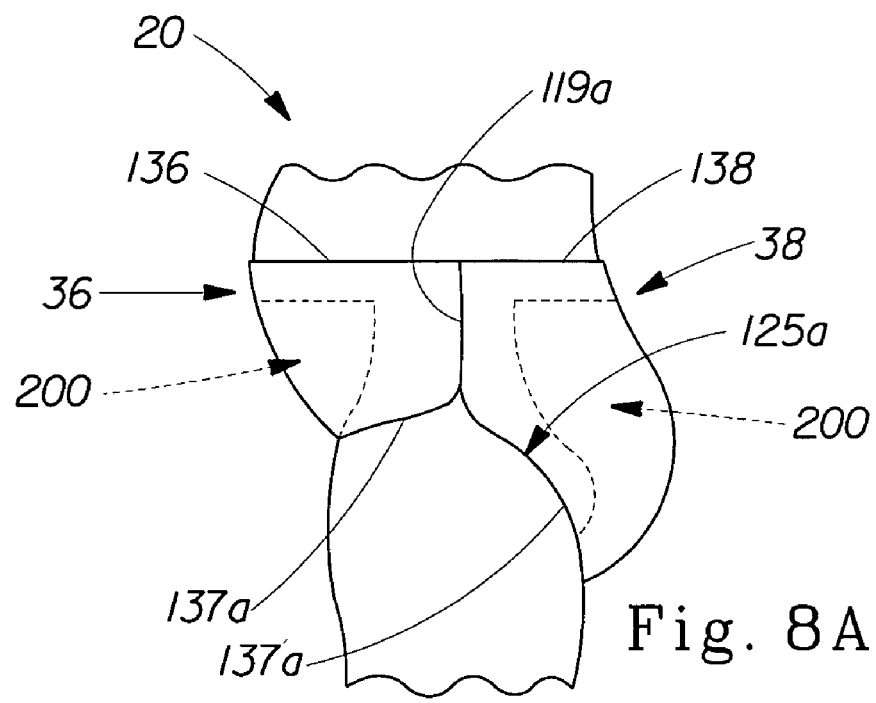
FIG. 8A is a simplified left side elevation view of an exemplary pull-on diaper showing the diaper worn about a lower torso of a wearer.
Figure 8B:
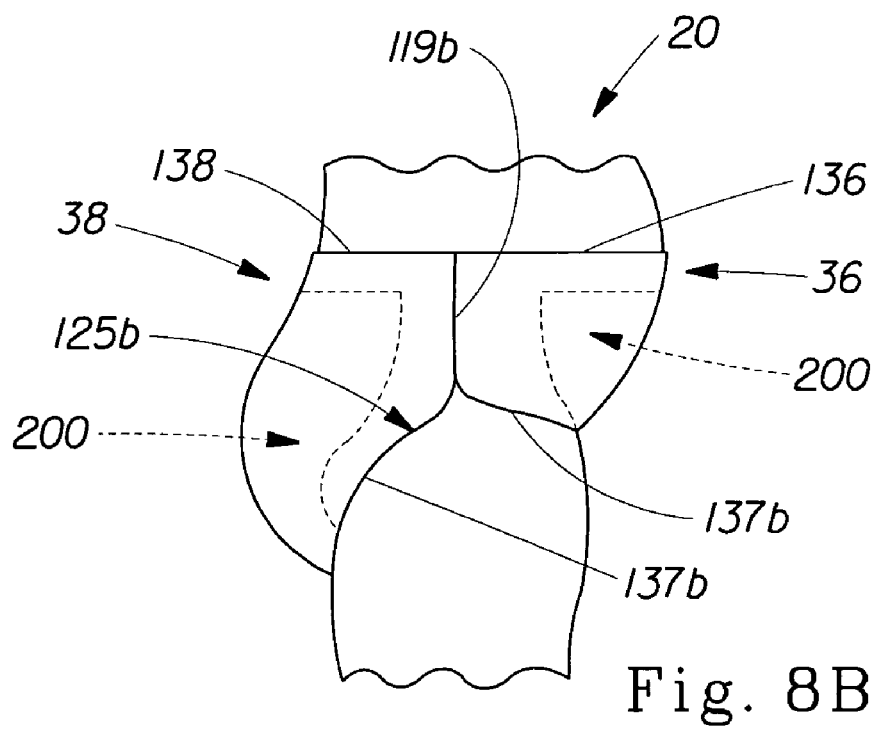
FIG. 8B is a simplified right side elevation view of the pull-on diaper illustrated in FIG. 8A showing the diaper worn about a lower torso of the wearer.
Figure 9:
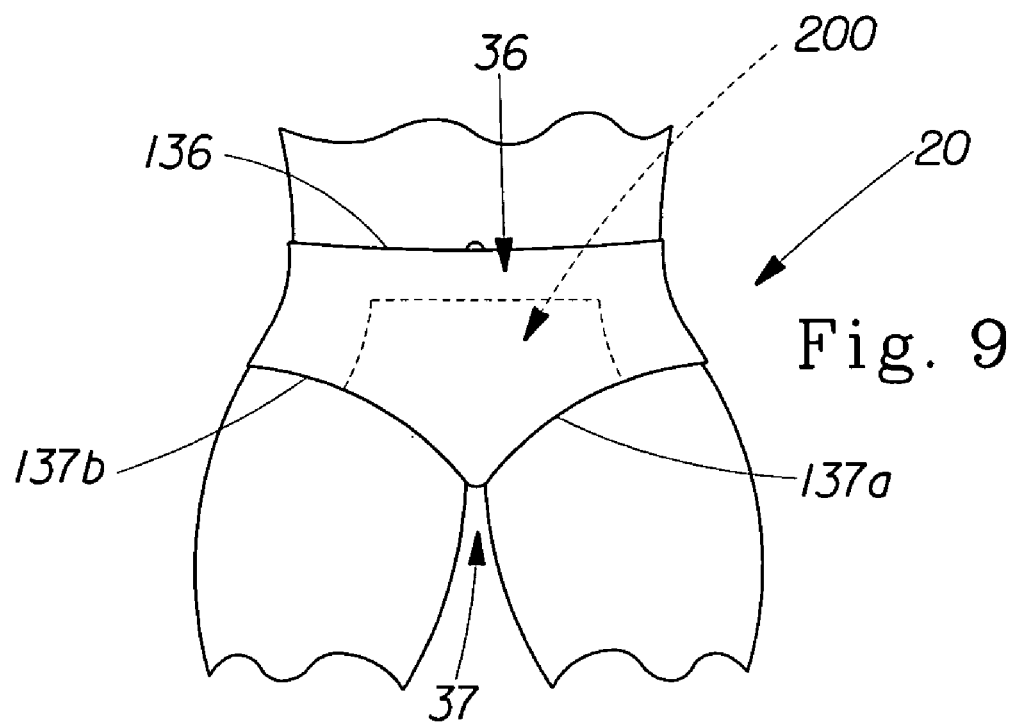
FIG. 9 is a front elevation view of the diaper illustrated in FIGS. 8A-B being worn about the lower torso of the wearer.
Figure 10:
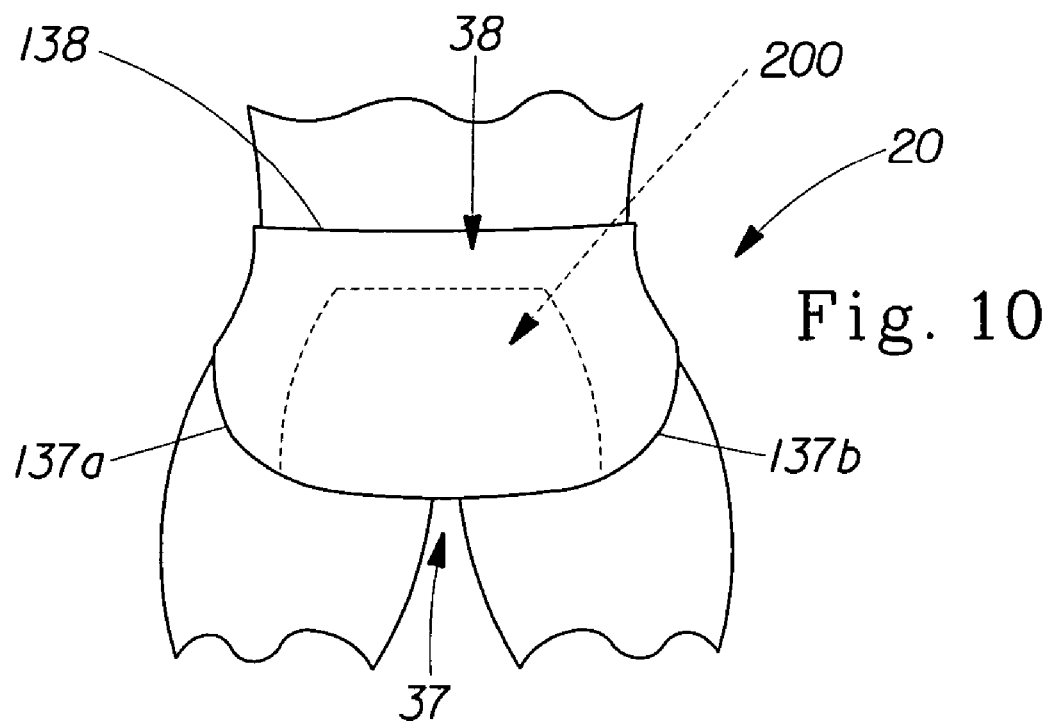
FIG. 10 is a back elevation view of the diaper illustrated in FIGS. 8A-B being worn about the lower torso of the wearer.

As shown in FIGS. 8-10, when the pull-on diaper 20 is worn on the lower torso of a wearer, the front waist edge 136 and the back waist edge 138 encircle the waist of the wearer while, at the same time, the chassis side edges 137a and 137b encircle the legs of the wearer, and thus define left and right leg openings 125a and 125b, respectively. The crotch region 37 is generally positioned between the legs of the wearer such that the absorbent assembly 200 extends from the front waist region 36 through the crotch region 37 to the back waist region 38.

Furthermore, as illustrated in FIGS. 1 and 8A-B, a garment may be preformed by the manufacturer to create a pull-on diaper or pant 20. Specifically, the diaper 20 includes left and right closed side interfaces 119a and 119b, each disposed at left and right side edge regions 145a and 145b, respectively, which are defined as regions adjacent, and including, the respective side edge 137a and 137b and being disposed in the waist regions 36 and 38. The side edge regions 145a and 145b can extend as longitudinally inward from front and back side edges 136 and 138 as desired. Moreover, the side edge regions 145a and 145b may terminate longitudinally inward from front and back side edges 136 and 138. The closed left side interface 119a is defined by an attachment between 1) the left side edge region 145a at a front left attachment zone 143a disposed in the front waist region 36, and 2) the left side edge region 145b at a back left attachment zone 150a disposed in the back waist region 38. Similarly, the closed right side interface 119b is defined by an attachment between 1) the right side edge region 145b at a front right attachment zone 143b disposed in the front waist region 36, and 2) the right side edge region 145b at a back attachment zone 150b disposed in the back waist region 38. The attachment zones 143a-b may or may not extend to the corresponding waist edges 136 and 138, and may or may not extend to the corresponding side edges 137a and 137b. Furthermore, one skilled in the art will appreciate that the attachment zones 143a-b could be closed using any permanent or refastenable closure member. The attachment zones 143a-b at the side edge regions 145a-b can be attached to form closed side interfaces 119a-b by buttressing and subsequently attaching the side edge 137a in the front and back waist regions 36 and 38, and side edge 137b in the front and back waist regions, respectively, either using a permanent or refastenable closure member, as illustrated in FIGS. 8A-B.

Figure 11:
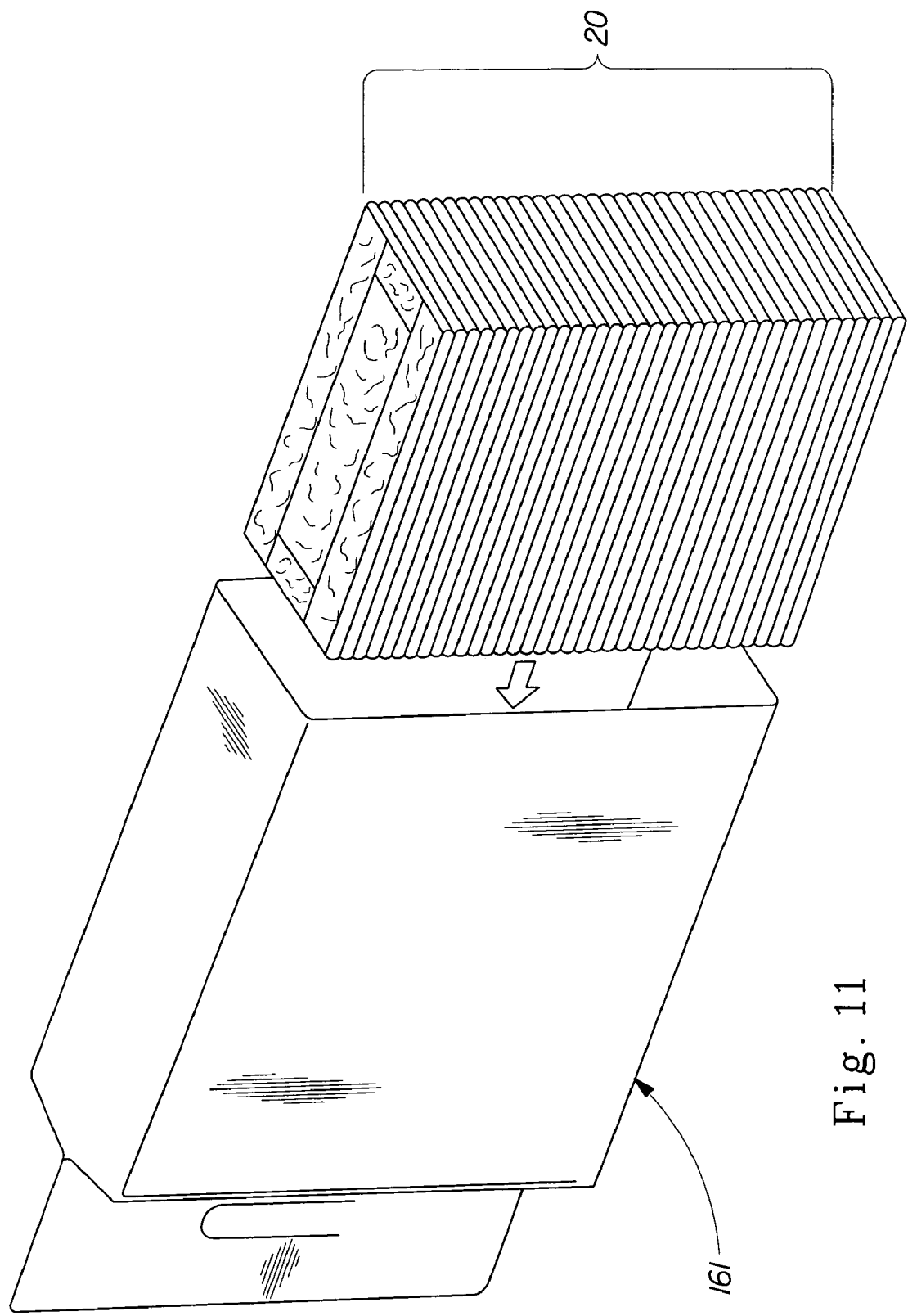
FIG. 11 is a schematic view of a plurality of prepackaged pull-on diapers constructed in accordance with the present invention.

Because the diaper 20 is configured as a pull-on diaper, both side interfaces 119a and 119b are pre-closed, meaning that the side interfaces 119a-b are closed prior to removal of the diaper 20 from its package 161, as illustrated in FIG. 11, and therefore prior to being donned on the wearer. The closed side interfaces 119a-b, in part, define the continuous, closed, left and right leg openings 125a and 125b, respectively, and a continuous, closed, waist opening 144, adapted to fit and gasket the wearer's legs and waist, respectively, as the diaper 20 is pulled up to the wearer's lower torso region. The side interfaces 119a-b can be formed into a closed configuration in accordance with any known techniques or methods known in the art. For instance, the interfaces 119a and 119b can be formed with a seam, which may include a bond formed by heat sealing such as ultrasonic bonding, high pressure bonding, RF (radio frequency) bonding, hot air bonding, heated point bonding, and the like as appreciated by one having ordinary skill in the art. Various suitable pant configurations are disclosed in U.S. Pat. No. 5,246,433 (issued on Sep. 21, 1993 to Margeret H. Hasse, et al); U.S. Pat. No. 5,569,234 (issued on Oct. 29, 1996 to Kenneth B. Buell, et al); U.S. Pat. No. 6,120,487 (issued on Sep. 19, 2000 to Gregory Ashton); U.S. Pat. No. 6,120,489 (issued on Sep. 19, 2000 to Larry Johnson, et al); U.S. Pat. No. 4,940,464 (issued on Jul. 10, 1990 to Paul T. Van Gompel); U.S. Pat. No. 5,092,861 (issued on Mar. 3, 1992 to Hironori Nomura et al); U.S. Pat. No. 5,897,545 (issued on Apr. 27, 1999 to Mark James Kline, et al); U.S. Pat. No. 5,957,908 (issued on Sep. 28, 1999 to Mark James Kline, et al); and U.S. Patent Publication No. 2003/0233082 A1 (published on Dec. 18, 2003 to Mark J. Kline, et al).

Alternatively, the closed side interfaces 119a-b can be formed as disclosed in U.S. Pat. No. 5,779,831 (issued on Jul. 14, 1998 to Christoph Schmitz); U.S. Pat. No. 5,772,825 (issued on Jun. 30, 1998 to Christoph Schmitz); U.S. Pat. No. 5,607,537 (issued on Mar. 4, 1997 to Larry Johnson, et al); U.S. Pat. No. 5,622,589 (issued on Apr. 22, 2997 to Larry Johnson, et al); U.S. Pat. No. 5,662,638 (issued on Sep. 2, 1997 to Larry Johnson, et al); U.S. Pat. No. 6,042,673 (issued on Mar. 28, 2000 to Larry Johnson, et al); and U.S. Pat. No. 6,726,792 (issued on Apr. 27, 2004 to Larry Johnson, et al). The aforementioned patents disclose various processing methods to provide absorbent pull-on diapers. One of the processes utilizes a final knife followed by a reciprocating tucker blade that pushes the pad from a horizontal orientation to a vertical orientation and a vacuum conveyor belt that holds the pad through a high pressure side seaming unit. The side seaming unit is followed by a slitter that trims the pant edges to provide a finished seam edge. An alternative method disclosed in the aforementioned patents involves cutting the pad in the final knife and bi-folding the pad collecting the pads in a "waterwheel" stacker (a rotary slotted wheel). The bonding is accomplished while the pad is held in place on the rotating wheel.

Figure 7A:
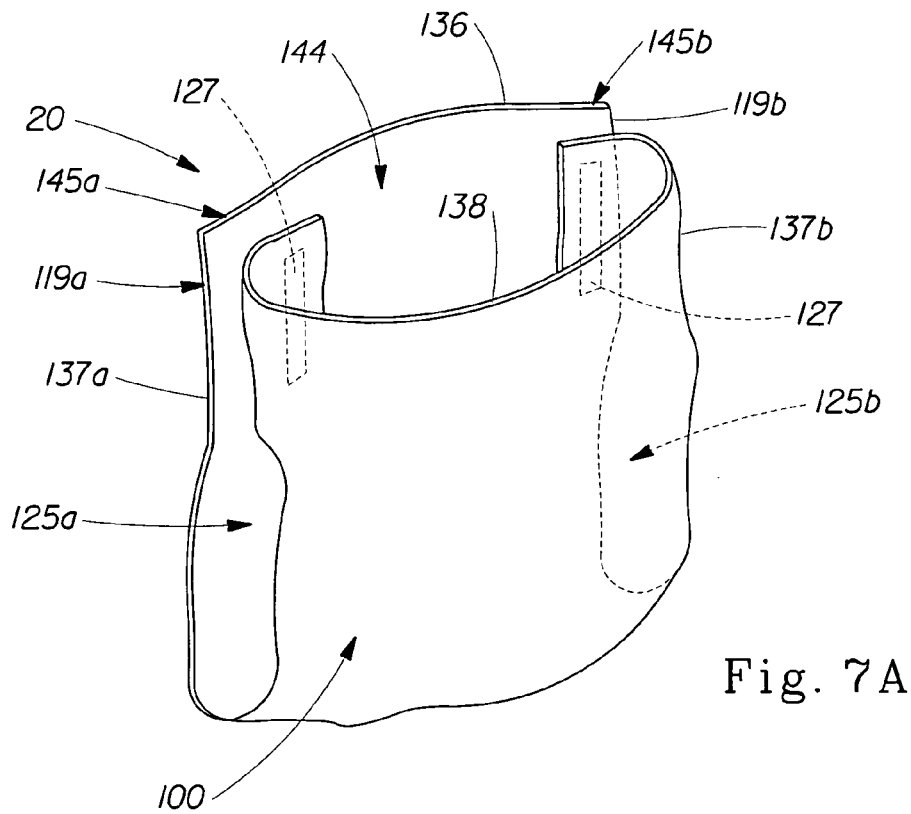
FIG. 7A is a schematic perspective view of the diaper illustrated in FIG. 1 configured as a pull-on diaper showing the side interfaces constructed in accordance with one embodiment of the present invention.

Alternatively, referring to FIGS. 1 and 7A, a left side edge region 145a (defined as a region adjacent the left side edge 137a and including the left side edge 137a) at the front left attachment zone 143a (i.e., in the front waist region 36) is overlapped with the left side edge region 145a at the back attachment zone 150a (i.e., in the back waist region 38) in an interior surface-to-exterior surface (or vice versa) configuration. Likewise, a right side edge region 145b (defined as a region adjacent the right side edge 119b and including the right side edge 119b) at the front right attachment zone 143b (i.e., in the front waist region 36) is overlapped with the right side edge region 145b at the back attachment zone 150b (i.e., in the back waist region 38) in an interior surface-to-exterior surface (or vice versa) configuration. Accordingly, the left and right side interfaces 119a and 119b can be closed by attaching the overlapping attachment zones 143 and 150 via any suitable permanent or refastenable closure member 127, such as a seam of the type described above, or an adhesive, a cohesive, a tab-and-slot configuration, or via hook-and-loop attachments. It should be appreciated that joining the side edge regions 145a and 145b causes the side edges 137a and 137b to correspondingly be joined indirectly via the side edge regions 145a and 145b.

Figure 7B:
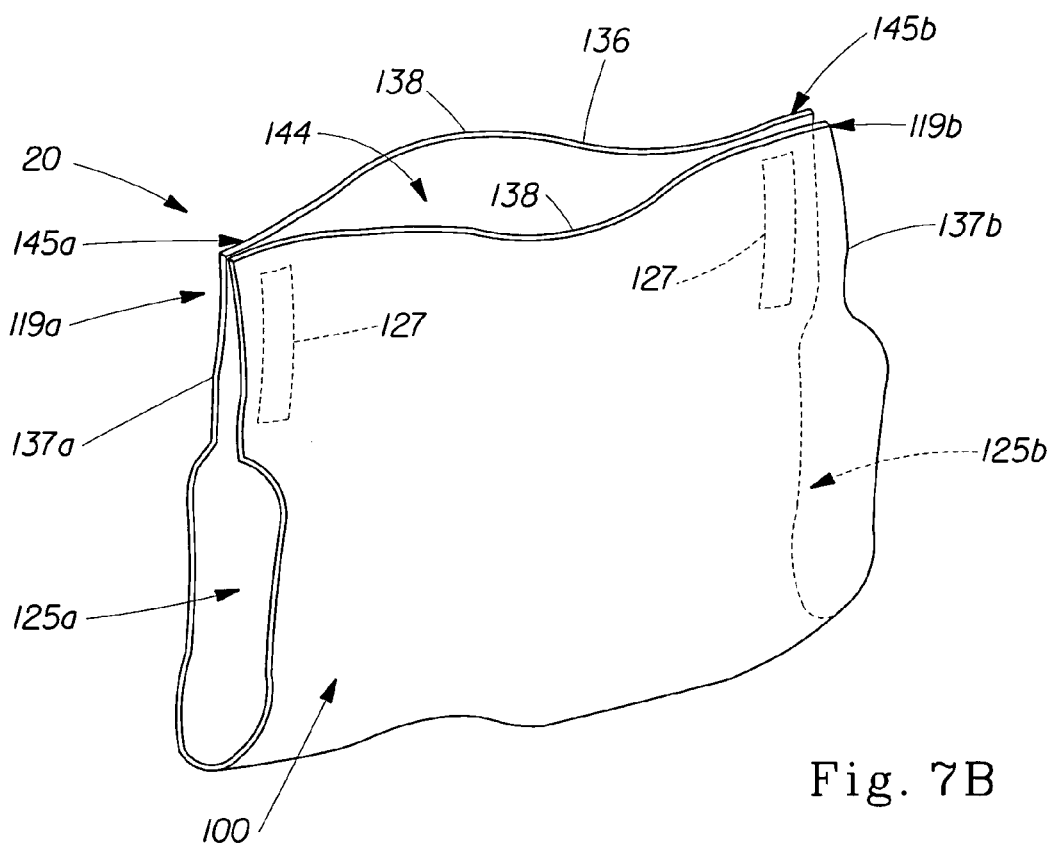
FIG. 7B is a schematic perspective view of the diaper illustrated in FIG. 1 configured as a pull-on diaper showing the side interfaces constructed in accordance with an alternative embodiment.

Alternatively, referring to FIGS. 1 and 7B, the closed side interfaces 119a and 119b are formed by bi-folding the chassis 100 such that the left and right side edge regions 145a-b, adjacent the front waist edge 136, overlap the left and right side edge regions 145a-b, respectively, adjacent the back waist edge 138 in an interior-to-interior surface configuration. In this configuration, the front waist edge 136 can be substantially aligned with the back waist edge 138 and the side edge 137a in the front and back waist regions can also be substantially aligned as can be the front and back waist regions of side edge 137b. The folded chassis 100 is then attached at the side edge regions 145a-b at the attachment zones 143 and 150, respectively (FIG. 1), using any suitable permanent or refastenable closure member 127, thereby forming a pull-on diaper defining continuous left and right leg openings 125a and 125b, respectively, and a continuous, closed, waist opening 144.

Figure 7C:
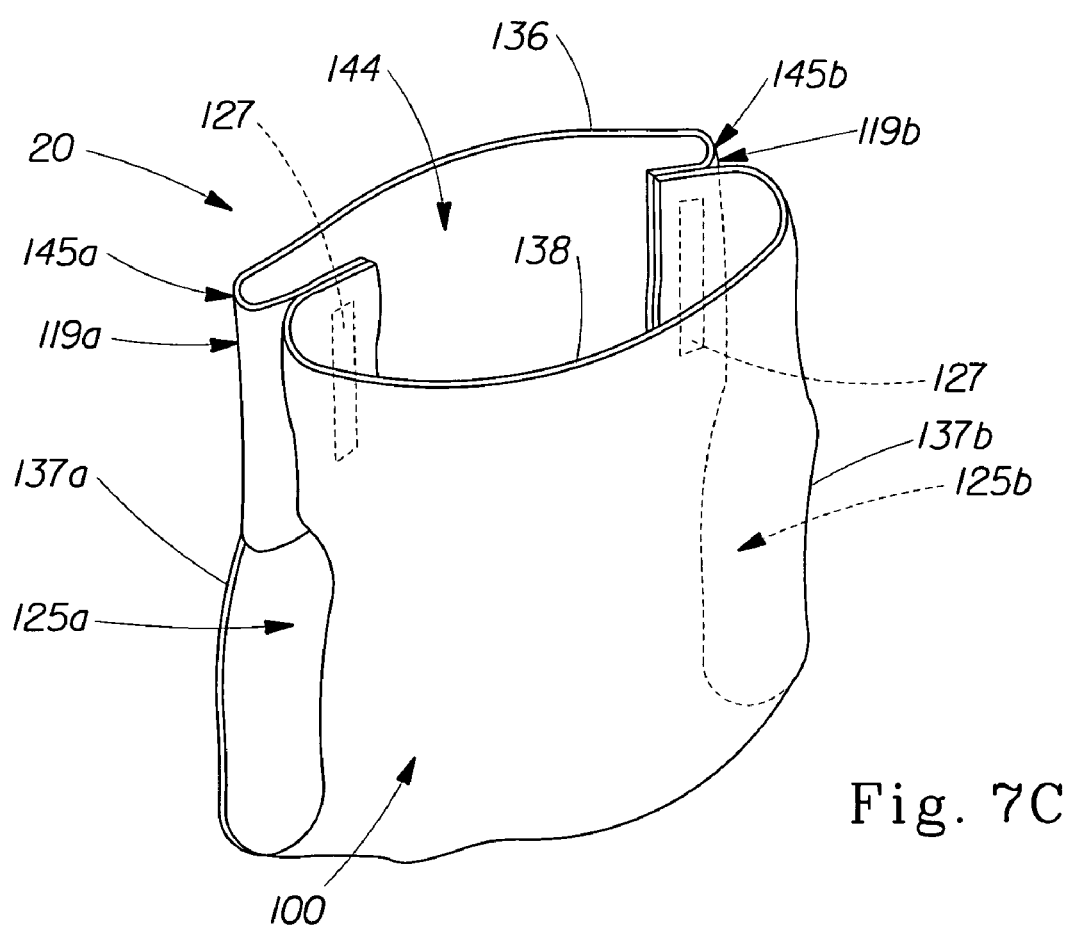
FIG. 7C is a schematic perspective view of the diaper illustrated in FIG. 1 configured as a pull-on diaper showing the side interfaces constructed in accordance with an alternative embodiment.

Alternatively still, referring to FIGS. 1 and 7C, the closed side interfaces 119a and 119b can be formed by bi-folding chassis 100 such that the left and right side edge regions 145a-b, adjacent the front waist edge 136, overlap the left and right side edge regions 145a-b, respectively, adjacent the back waist edge 138 in an exterior-to-exterior surface configuration. In this configuration, the front end edge 136 can be substantially aligned with the back end edge 138. The folded chassis 100 is then attached at the side edge regions 145a-b at the attachment zones 143 and 150, respectively (FIG. 1), using any suitable permanent or refastenable closure member 127, thereby forming a pull-on diaper defining continuous left and right leg openings 125a and 125b, respectively, and a continuous, closed, waist opening 144.

Furthermore, one having ordinary skill in the art will appreciate that the side interfaces 119a-b can be closed via a refastenable closure member that can be nondestructively opened and refastened. Examples of refastenable closure members include hook-and-loop fasteners, snaps, tab-slot fasteners, cohesives, and the like.

Examples of closure members are described in U.S. Pat. No. 6,432,098 (issued Aug. 13, 2002 to Kline et al); U.S. Pat. No. 6,880,211 (issued Apr. 19, 2005 to Jackson et al); and U.S. Patent Publication No. 2003/0233082 (published Dec. 18, 2003 to Kline et al).

The present invention therefore recognizes that a plurality of pull-on diapers 20 can be pre-formed having the closed side interfaces 119a and 119b and packaged, and subsequently delivered to a user to prevent the need for the user (which could be the wearer) to close the side edges 137a and 137b prior to securing the diaper 20 on the wearer. Accordingly, referring to FIG. 11, the present invention includes the method of providing a plurality of pull-on diapers 20 of the type described above, placing the diapers 20 into a closed package or other containment apparatus 161 that retains the diapers 20. Accordingly, when the end user opens the packaging 161, the pull-on diaper can be donned on the wearer more easily than conventional taped diapers.

The term "pre-closed" refers to an absorbent article that can be closed by the end user and formed into a pant-like garment prior to applying the garment to the wearer. The term "pre-closed" also encompasses an absorbent article that has been formed into a pant-like garment in the packaging 161 such that the end user receives the article as a pant-like garment that can be directly applied to the wearer.

Description of the Chassis

Referring also to FIGS. 12-17, the chassis 100 is shown laid out flat before the side flaps 147a and 147b are formed by folding portions of the chassis 100 laterally inward, i.e., toward the longitudinal axis 42, to form both the respective side flaps 147a and 147b and the side edges 137a and 137b of the chassis 100 as shown in FIGS. 1-6. In this condition of being laid out flat, the chassis 100 has a longitudinally extending left outer side edge 155a and a laterally opposing and longitudinally extending right outer side edge 155b. Both of these chassis outer side edges extend longitudinally between the front waist edge 136 and the back waist edge 138. As is described in more detail below, when the side flaps 147a and 147b are formed by folding portions of the chassis 100 laterally inward, the outer side edges 155a and 155b of the chassis form respective proximal edges 157a and 157b of the side flaps 147a and 147b.

The chassis 100 includes a water-impermeable backsheet 26 defining an exterior surface that is intended to be placed toward clothing that is worn over the pull-on diaper 20. The backsheet 26 can be formed from films of polyethylene and other polyolefins, or can alternatively be formed as multilayer structures, such as laminates of a film and a nonwoven, or alternatively as a dual layer nonwoven laminate as understood by one having ordinary skill in the art. A laminate backsheet can be oriented with the nonwoven disposed exteriorly to provide the feel and appearance of a more cloth-like outermost layer than would be provided by using the film as the outermost layer.

Figure 12:
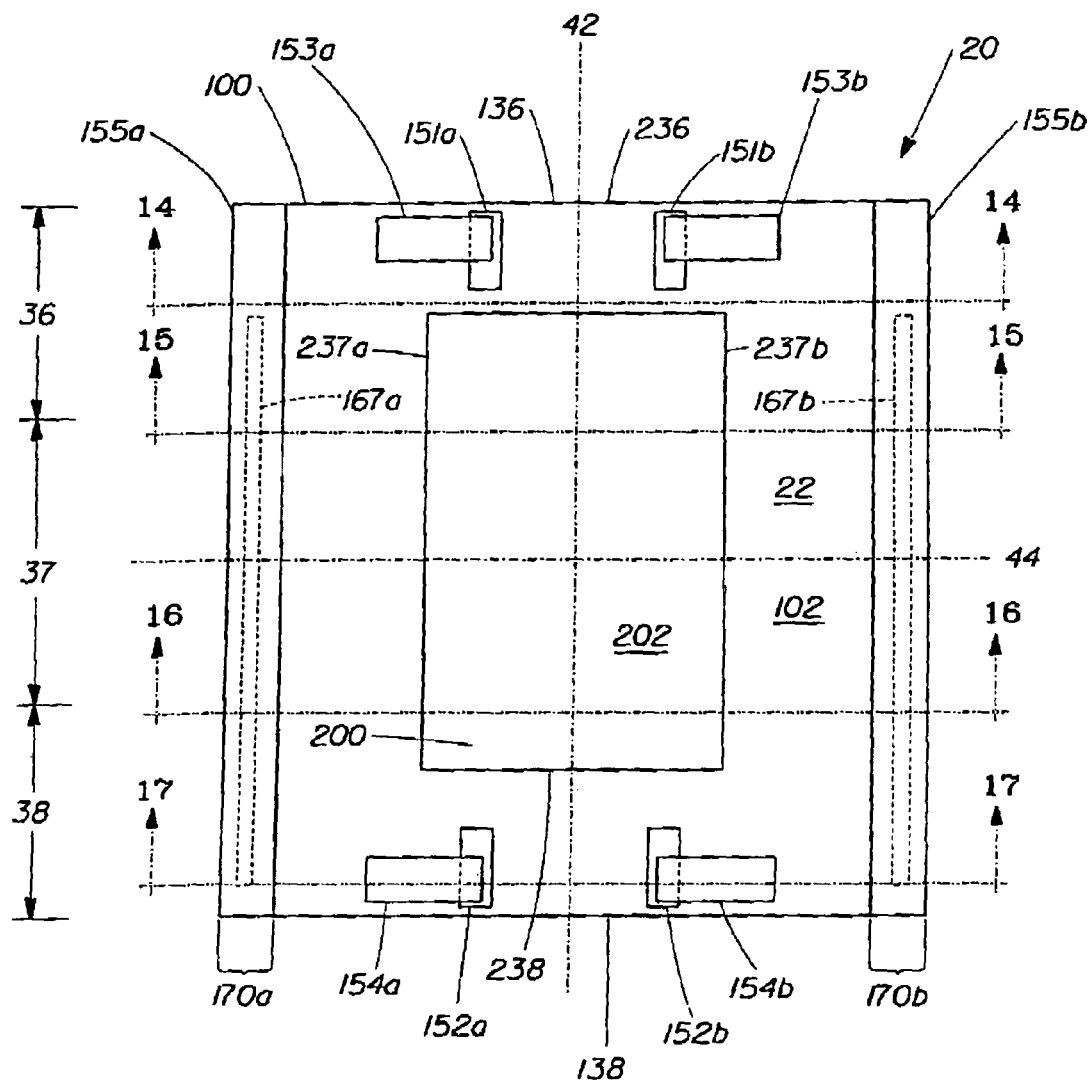
FIG. 12 is a plan view of a pull-on diaper constructed in accordance with an alternative embodiment, with the interior portion of the diaper that faces inwardly toward the wearer and contacts the wearer shown facing the viewer, shown in its flat, uncontracted state (i.e., without the contraction induced by elastic members) before side flaps are formed by folding portions of the chassis laterally inward.
Figure 13:
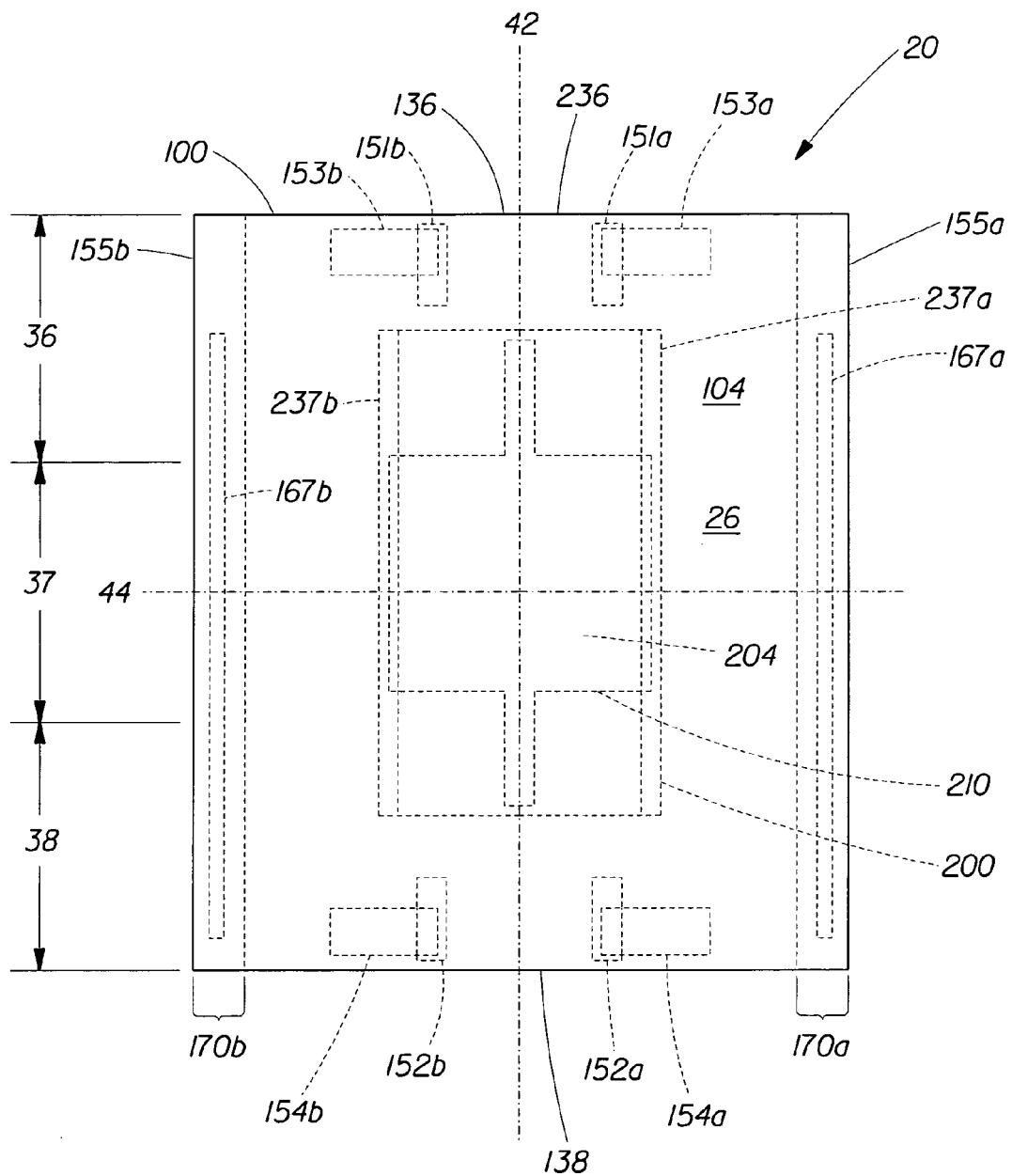
FIG. 13 is a plan view of the diaper illustrated in FIG. 12 in its flat, uncontracted state, with the exterior portion of the diaper that faces outwardly away from the wearer shown facing the viewer.
Figure 14:
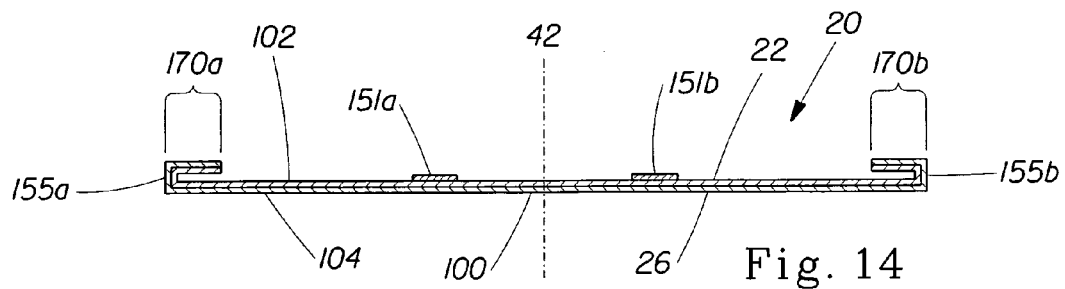
FIG. 14 is a section view of the diaper illustrated in FIG. 12 taken along line 14-14.
Figure 15:
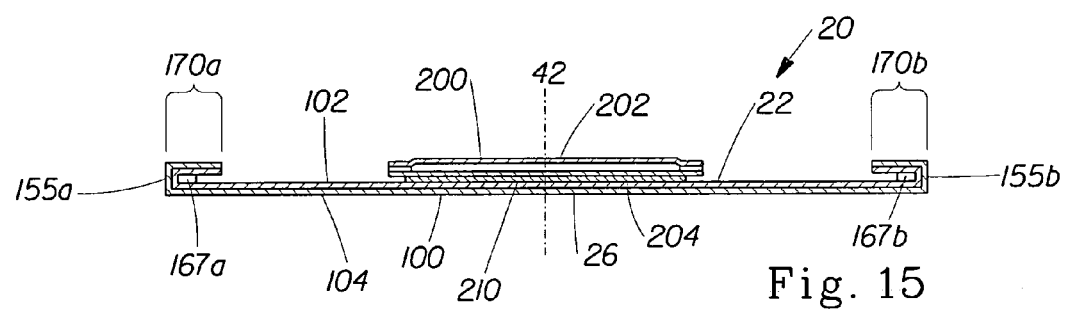
FIG. 15 is a section view of the diaper illustrated in FIG. 12 taken along line 15-15.
Figure 16:
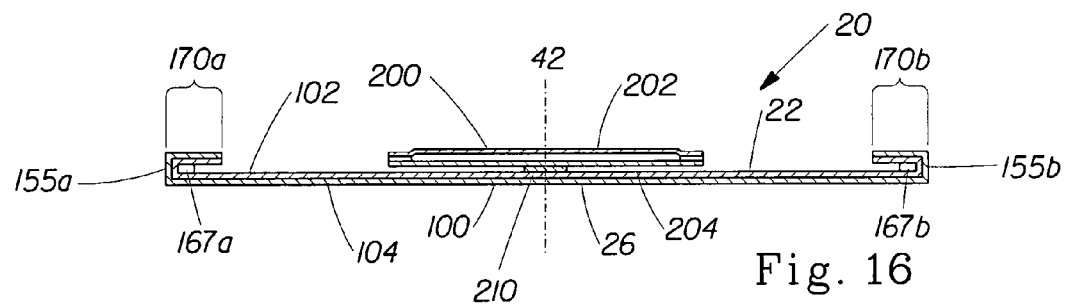
FIG. 16 is a section view of the diaper illustrated in FIG. 12 taken along line 16-16.
Figure 17:
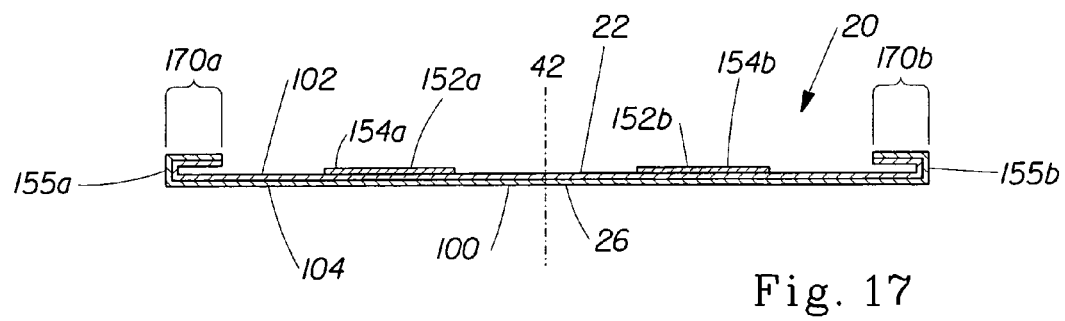
FIG. 17 is a section view of the diaper illustrated in FIG. 12 taken along line 17-17.

The chassis 100 can further include an inner liner 22 attached to the backsheet 26. As illustrated in FIGS. 12-13, the inner liner 22 can extend to the same width and the same length as the backsheet 26. The inner liner 22 can form a portion of the interior surface 102 of the chassis 100 that is intended to be placed against the body of the wearer. Accordingly, the inner liner 22 can be formed of a soft material that will not irritate the skin of the wearer, and can serve to isolate the skin of the wearer from a portion of the backsheet 26. This may be desired, for instance, when the pull-on diaper 20 is worn under conditions in which contact between the skin and a backsheet film could be uncomfortable. Many suitable materials for the inner liner 22 are well known in the art, including rayon and synthetic nonwovens such as spunbonded or carded polypropylene, polyethylene or polyester.

In accordance with an alternative embodiment, one or more of the edges of the inner liner 22 can lie inward of the edges of the backsheet 26. For example, referring to FIG. 1, only the portions of the inner liner 22 lying in the gaps between the front edge 236 of the absorbent assembly 200 and the front waist edge 136 of the chassis 100 and between the back edge 238 of the absorbent assembly 200 and the back waist edge 138 of the chassis 100 are exposed, while the remainder of the inner liner 22 is covered by the absorbent assembly 200 and the side flaps 147a and 147b. Therefore, a laterally extending strip of the inner liner 22 disposed in the gap in the front waist region 36 and a similar laterally extending strip of the inner liner 22 disposed in the gap in the back waist region 38 can suffice to isolate the skin of the wearer from the backsheet 26 in these two gaps.

As shown in FIGS. 1-6, the chassis 100 includes longitudinally extending and laterally opposing side flaps 147a and 147b that are disposed on the interior portion of the diaper 20. The side flaps 147a and 147b can be formed by folding portions of the chassis 100 laterally inward to form both the respective side flaps 147a and 147b and the side edges 137a and 137b of the chassis 100. Alternatively, the side flaps 147a and 147b can be formed by attaching an additional layer or layers to the chassis 100 at or adjacent to each of the respective side edges 137a and 137b of the chassis 100.

Portions of a film backsheet 26 that are folded laterally inward to form the side flaps can contact the skin of a wearer during the use of the pull-on diaper 20. However, the alternating ridges and valleys in such a film backsheet that has been deformed in order to make it extensible can provide channels through which air can pass to alleviate any concern regarding such contact of the film backsheet with the skin.

In embodiments in which portions of the chassis 100 are folded laterally inward to form the side flaps 147a and 147b, the chassis 100 can simply be folded loosely or can be creased along a portion of each of its side edges 137a and 137b. For example, it may be desirable to form creases along portions of the side edges 137a and 137b in the crotch region 37 in order to impart a more finished appearance to the diaper 20. Alternatively or in addition to creasing, a portion of each of the folded side flaps 147a and 147b adjacent to the side edges 137a and 137b can be attached to the interior surface 102 of the chassis 100 to achieve a similar result.

The left side flap 147a defines a proximal edge 157a and the right side flap 147b defines a proximal edge 157b. In the exemplary diaper 20 shown in FIG. 1, the proximal edge 157a and the proximal edge 157b lie laterally inward of the respective left side edge 237a and right side edge 237b of the absorbent assembly 200, and the left side flap 147a and the right side flap 147b thus overlap the absorbent assembly 200. Such an overlapped configuration may be desirable in order to impart a more finished appearance to the diaper 20 than that imparted by a non-overlapped configuration. Alternatively, the left side flap 147a and the right side flap 147b do not overlap the absorbent assembly 200, for instance when the proximal edge 157a and the proximal edge 157b lies laterally outward of the respective left side edge 237a and right side edge 237b of the absorbent assembly 200.

Referring again to FIG. 1, the left side flap 147a and the right side flap 147b extend the full length of the chassis 100 between the front waist edge 136 and the back waist edge 138. Such a full length configuration may be desirable in order to minimize the amount of waste material and the difficulty associated with the manufacture of the pull-on diaper 20, especially when the method used to manufacture the diaper 20 requires the introduction of the material or materials for the chassis 100 in the form of a continuous web or multiple continuous webs. Alternatively, the side flaps can be shorter and extend less than the full distance between the front waist edge 136 and the back waist edge 138. Such a shorter configuration may be desirable in order to minimize the total amount of material used in the manufacture of the pull-on diaper 20.

Each of the side flaps 147a and 147b is attached to the interior surface 102 of the chassis 100 in attachment zones located in the front waist region 36 and in the back waist region 38. For example, the side flaps 147a and 147b are attached to the interior surface 102 of the chassis 100 in front longitudinally oriented adhesive attachment zones 151 and back longitudinally oriented adhesive attachment zones 152 (more clearly visible in FIG. 12). In particular, the left side flap 147a is attached to the interior surface 102 of the chassis 100 in opposing longitudinally oriented adhesive attachment zones 151a and 152a. Attachment zone 151a is disposed adjacent the proximal edge 157a of left side flap 147a near the front waist edge 136, and attachment zone 152a is disposed adjacent the proximal edge 157a near the back waist edge 138. Similarly, the right side flap 147b is attached to the interior surface 102 of the chassis 100 in opposing longitudinally oriented adhesive attachment zones 151b and 152b. Attachment zone 151b is disposed adjacent the proximal edge 157b of right side flap 147b near the front waist edge 136, and attachment zone 152b is disposed adjacent the proximal edge 157b near the back waist edge 138. The adhesive attachment zones can have equal areas or can be unequal in area. For example, the front longitudinally oriented adhesive attachment zones 151a and 151b can be of one size and the back longitudinally oriented adhesive attachment zones 152a and 152b can be of another size.

Additionally, or alternatively, the side flaps 147a and 147b can be attached to front and back laterally oriented adhesive attachment zones 153 and 154, respectively. Specifically, the left side flap 147a is attached to the interior surface 102 of the chassis 100 in opposing laterally oriented adhesive attachment zone 153a and 154a. Adhesive zone 153a is disposed adjacent the front waist edge 136 and adhesive attachment zone 154a is disposed adjacent the back waist edge 138. Similarly, the right side flap 147b is attached to the interior surface 102 of the chassis 100 in opposing laterally oriented adhesive attachment zones 153b and 154b. Attachment zone 153b is disposed adjacent the front waist edge 136 and attachment zone 154b is disposed adjacent to the back waist edge 138. The adhesive attachment zones can have equal areas or can be unequal in area. For example, the front laterally oriented adhesive attachment zones 153a and 153b can be of one size and the back laterally oriented adhesive attachment zones 154a and 154b can be of another size.

Alternatively, each attachment zone can extend laterally across the full width of the respective side flap. For example, a laterally oriented adhesive attachment zone can extend laterally from the chassis left side edge 137a to the left side flap edge 157a and thereby attach the entire width of the left side flap 147a adjacent to the front waist edge 136 to the interior surface 102 of the chassis 100. In embodiments in which the front edge 236 or the back edge 238 of the absorbent assembly 200 coincides with the respective front waist edge 136 or back waist edge 138 of the chassis 100 and the side flaps 147a and 147b overlap the absorbent assembly 200, the side flaps 147a and 147b can be attached to the absorbent assembly 200 instead of, or in addition to, being attached to the interior surface 102 of the chassis 100.

Between the attachment zones, the proximal edges 157a and 157b of the side flaps 147a and 147b remain unattached to the interior surface 102 of the chassis 100 or to the absorbent assembly 200. Also between the attachment zones, each side flap preferably includes a longitudinally extensible flap elastic member that is attached adjacent to the proximal edge of the side flap by any of many well-known means. Each such flap elastic member can be attached over its entire length or over only a portion of its length. For example, such a flap elastic member can be attached only at or near its longitudinally opposing ends and can be unattached at the middle of its length. Such a flap elastic member can be disposed in the crotch region 37 and can extend into one or both of the front waist region 36 and the back waist region 38. For example, in the exemplary chassis 100 shown in FIG. 1, an elastic strand 167a is attached adjacent to the proximal edge 157a of the left side flap 147a and extends into both the front waist region 36 and the back waist region 38. Similarly, an elastic strand 167b is attached adjacent to the proximal edge 157b of the right side flap 147b and extends into both the front waist region 36 and the back waist region 38.

Each flap elastic member can be enclosed inside a folded hem. For example, in the exemplary chassis 100 shown in FIGS. 4 and 5, the elastic strand 167a is enclosed inside a hem 170a formed adjacent to the proximal edge 157a of the left side flap 147a and the elastic strand 167b is enclosed inside a hem 170b formed adjacent to the proximal edge 157b of the right side flap 147b. Alternatively, the flap elastic member can be sandwiched between two layers of the chassis, e.g., between the layers of a laminate backsheet or between a backsheet and an inner liner. As another alternative, the flap elastic member can be attached on a surface of the chassis 100 and remain exposed.

Figure 18:
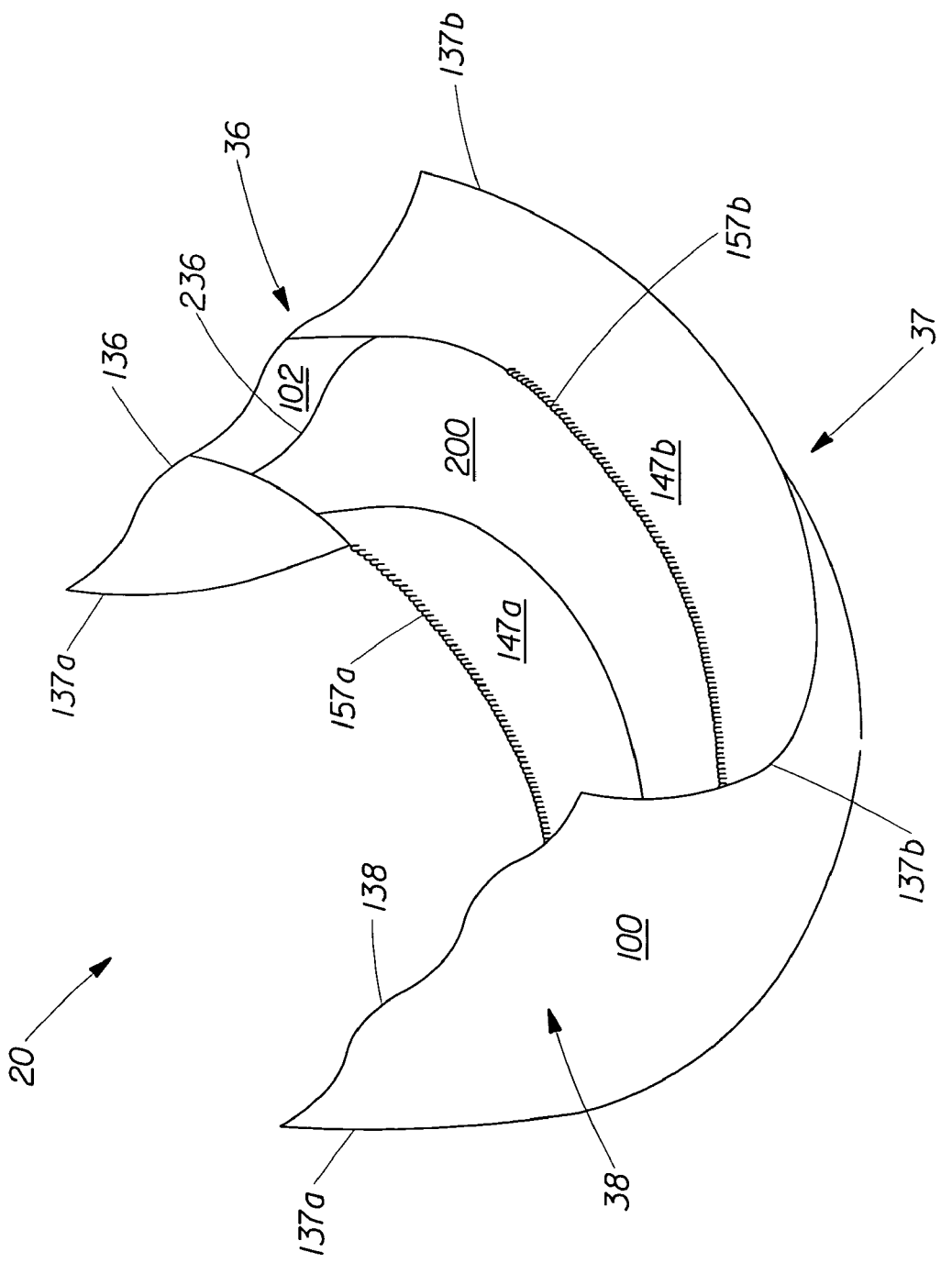
FIG. 18 is a perspective view of a pull-on diaper, with the interior portion of the diaper that faces inwardly toward the wearer and contacts the wearer shown facing upward, in which the diaper is shown in its contracted state prior to being configured into a pull-on diaper (i.e., with the contraction induced by elastic members)

When stretched, the flap elastic member disposed adjacent each side flap edge allows the side flap edge to extend to the flat uncontracted length of the chassis 100 as shown in FIG. 1. When allowed to relax, the flap elastic member contracts to gather the portion of the side flap edge along which the flap elastic member is attached and thereby make the relaxed length of the side flap edge less than the flat uncontracted length of the chassis. For example, when the exemplary diaper 20 is in a relaxed condition as shown in FIG. 18, the elastic strand 167a contracts to gather the proximal edge 157a of the left side flap 147a and the elastic strand 167b contracts to gather the proximal edge 157b of the right side flap 147b. The contractive forces of the elastic strands 167a and 167b are transmitted at the respective front attachment zones 151a and 151b to the interior surface 102 of the chassis 100 at the front waist region 36. Similarly, the contractive forces of the elastic strands 167a and 167b are transmitted at the respective back attachment zones 152a and 152b to the interior surface 102 of the chassis 100 at the back waist region 38. These contractive forces pull the front waist region 36 and the back waist region 38 toward each other and thereby bend the diaper 20 into a "U" shape in which the interior of the "U" shape is formed by the portions of the diaper 20 that are intended to be placed toward the body of the wearer. Because the proximal edge 157a remains free between the attachment zones 151a and 152a, the contractive force of the elastic strand 167a lifts the proximal edge 157a away from the interior surface 102 of the chassis 100. Similarly, because the proximal edge 157b remains free between the attachment zones 151b and 152b, the contractive force of the elastic strand 167b lifts the proximal edge 157b away from the interior surface 102 of the chassis 100. As shown in FIG. 19, this lifting of the proximal edges 157a and 157b when the diaper 20 is in the relaxed condition lifts the side flaps 147a and 147b into position to serve as side barriers adjacent to the side edges 237a and 237b of the absorbent assembly 200.

When the diaper 20 is worn, the relaxed "U" shape generally conforms to the body of the wearer such that the front waist region 36 and the back waist region 38 encircle the waist and the legs of the wearer. When the pull-on diaper 20 is worn in this manner, the elastic strands 167a and 167b tend to hold the lifted proximal edges 157a and 157b of the side flaps 147a and 147b in contact with the body of the wearer and thereby form seals to help prevent the leakage of deposited bodily waste out of the pull-on diaper 20. The lateral spacing of the lifted proximal edges 157a and 157b is selected to allow the deposit of bodily wastes from the lower torso of the wearer into the space between the lifted side flaps 147a and 147b and thereby directly onto the absorbent assembly 200. The width of each of the side flaps 147a and 147b in effect becomes its height when the free portion of its proximal edge 157a and 157b, respectively, is lifted and the side flap serves as a side barrier to leakage. This height preferably is selected to allow the lifted proximal edges 157a and 157b to fit into the leg creases of the body of the wearer at the same time as the absorbent assembly 200 is held in contact with the body.

Figure 2:
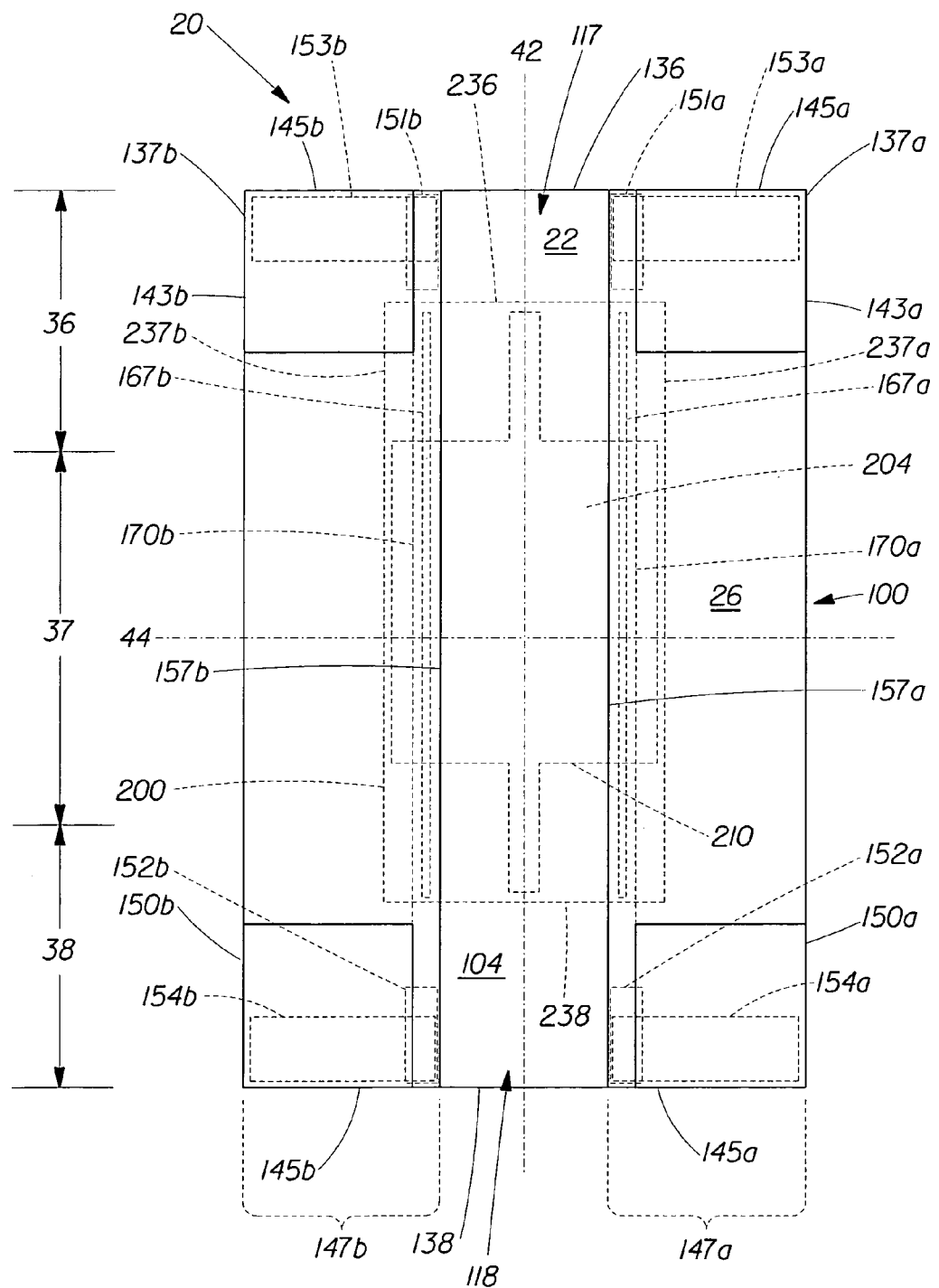
FIG. 2 is a plan view of the absorbent article illustrated in FIG. 1 in its flat, uncontracted state, with the exterior portion of the diaper that faces outwardly away from the wearer shown facing the viewer.

As illustrated in FIGS. 1-2, the chassis 100 can have a generally rectangular shape, which may be desirable in order to minimize the amount of waste material and the difficulty associated with the manufacture of the pull-on diaper 20. Alternatively, the chassis side edges 137a and 137b may not be straight, but instead can be curved and/or notched, thereby giving an overall shape in plan view of an hourglass or of an "I" to the pull-on diaper 20. Such a non-rectangular configuration may be desirable in order to impart a tailored appearance to the pull-on diaper 20 when it is worn, and further to impart an impression that the pull-on diaper 20 will fit comfortably between the legs of a wearer. Any one of many well-known techniques can be used to form a non-rectangular configuration of the chassis. For example, the chassis 100 can be made narrower in the crotch region 37 than at the waist edges 136 and 138 by removing laterally distal portions from the chassis 100 to make its lateral dimension at and adjacent to the lateral axis 44 smaller than its lateral dimension at and adjacent to the front waist edge 136 and smaller than its lateral dimension at and adjacent to the back waist edge 138. Alternatively, a portion of each of the side edges 137a and 137b can be folded laterally inward in order to achieve the same result. Such folded portions of the side edges 137a and 137b can be creased or attached, or both creased and attached, in order to prevent their unfoldment.

Figure 19A:
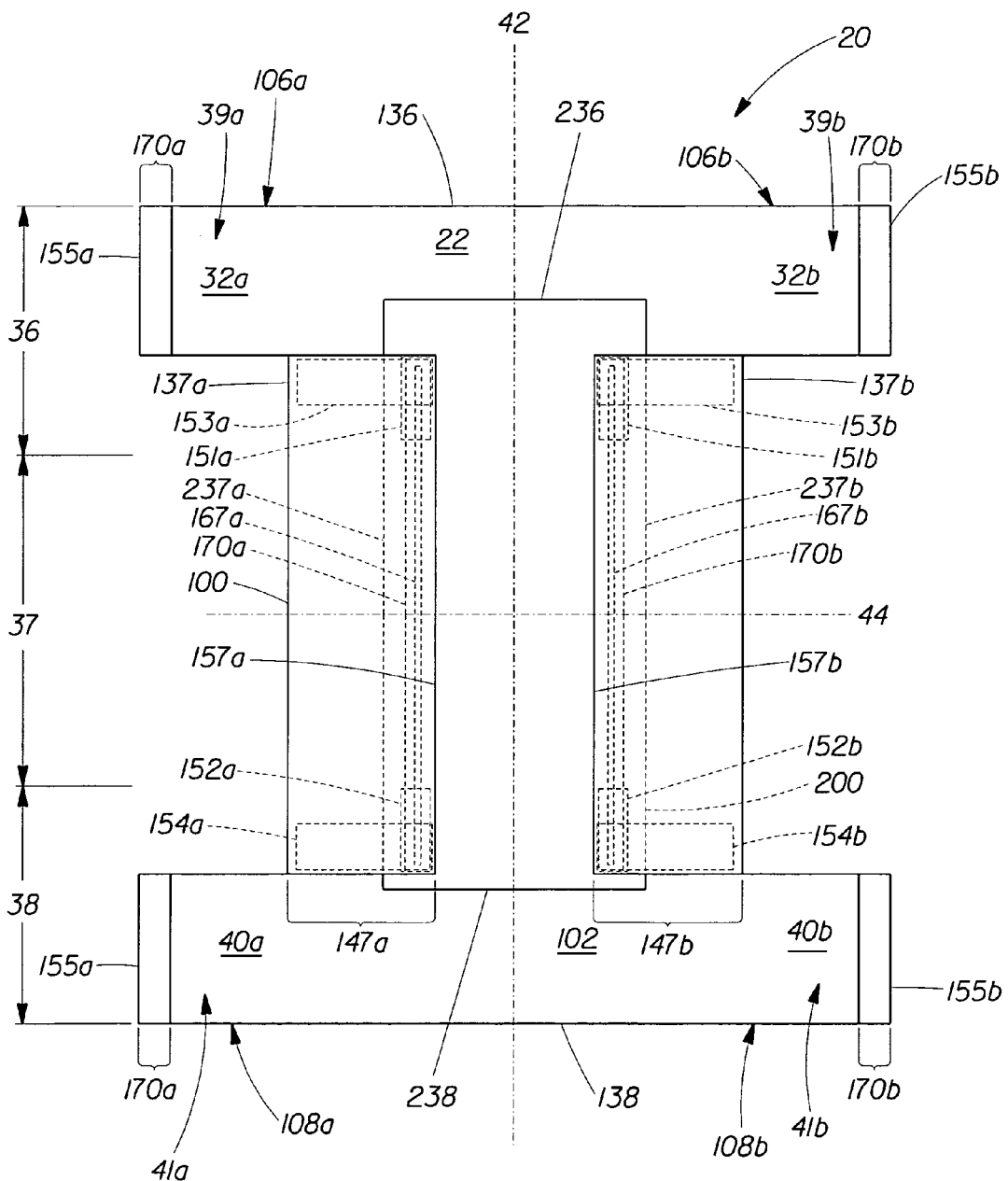
FIG. 19A is plan view of a pull-on diaper constructed in accordance with yet another alternative embodiment with the diaper shown in its flat, uncontracted state (i.e., without the contraction induced by elastic members) in which portions of the chassis are left laid out flat when other portions are folded laterally inward to form side flaps in an "I" configuration.

Referring to FIG. 19A, one exemplary non-rectangular configuration of the chassis 100 is shown, in which portions of the chassis extending laterally between the outer side edges and the respective side edges in one or both of the waist regions are left laid out flat when other portions are folded laterally inward to form the side flaps 147a and 147b. For instance, the portions 106a and 106b extending longitudinally from the front waist edge 136 toward the lateral axis 44 in the front waist region 36 and extending laterally between each of the outer side edges 155a and 155b and the respective side edges 137a and 137b can be left laid out flat. Similarly, the portions 108a and 108b extending longitudinally from the back waist edge 138 toward the lateral axis 44 in the back waist region 38 and extending laterally between each of the outer side edges 155a and 155b and the respective side edges 137a and 137b can be left laid out flat. Other portions extending longitudinally between the portions that remain unfolded and through the crotch region 37 can be folded laterally inward to form the side flaps 147a and 147b. The portions 106a and 106b and the portions 108a and 108b form side panels that project laterally outward from each of the waist regions of the diaper. These side panels 106a and 106b project laterally outward beyond the inward-folded portions and impart an "I"-shape to the pull-on diaper 20. It is not necessary that portions 106 and 108 remain unfolded at both ends as illustrated. For example, in some embodiments, the portions 106a and 106b in the front waist region 36 can alternatively remain unfolded and only the portions 108a and 108b in the back waist region 38 can be folded laterally inward, or vice versa. In some embodiments, portions 106 and 108 may be disposed laterally inward and then unfolded by separating the portion from the side flap along a frangible region.

In this embodiment, portions 106a-b and 108a-b define front and back side panels 32a-b and 40a-b, respectively, that can be pleated as described in more detail below to provide a more comfortable and contouring fit by initially conformably fitting the pull-on diaper 20 to the wearer and sustaining this fit throughout the time of wear well past when the pull-on diaper 20 has been loaded with exudates since pleated side panels will allow the sides of the pull-on diaper 20 to expand and contract. The side panels 32 and 40 may also provide more effective application of the pull-on diaper 20 because even if the elasticized side panel 32 is pulled farther than the other as the pull-on diaper is being applied onto the wearer, the pull-on diaper 20 will "self-adjust" during wear. Closed side interfaces 119a and 119b can thus be created by pre-closing the side panel 32a to side panel 40a adjacent the outer side edge 155a, and by pre-closing the side panel 32b to side panel 40b adjacent the outer side edge 155b, using any known closure member. More particularly, each side panel 32a-b and 40a-b defines a corresponding side panel region 39a-b and 41a-b, respectively, disposed adjacent, and including, the corresponding longitudinally extending side edge. The side panel regions 39a and 41a, and regions 39b and 41b, can be attached via any suitable refastenable or permanent closure member as described above to form the closed side interfaces 119a-b.

An "I"-shaped non-rectangular configuration of the chassis 100 can be alternatively provided by forming the chassis 100 in the "I"-shape and attaching an additional layer or layers to the interior surface of the chassis 100 at or adjacent to each of the side edges 137a and 137b of the chassis 100 to form the respective side flaps 147a and 147b.

Figure 19B:
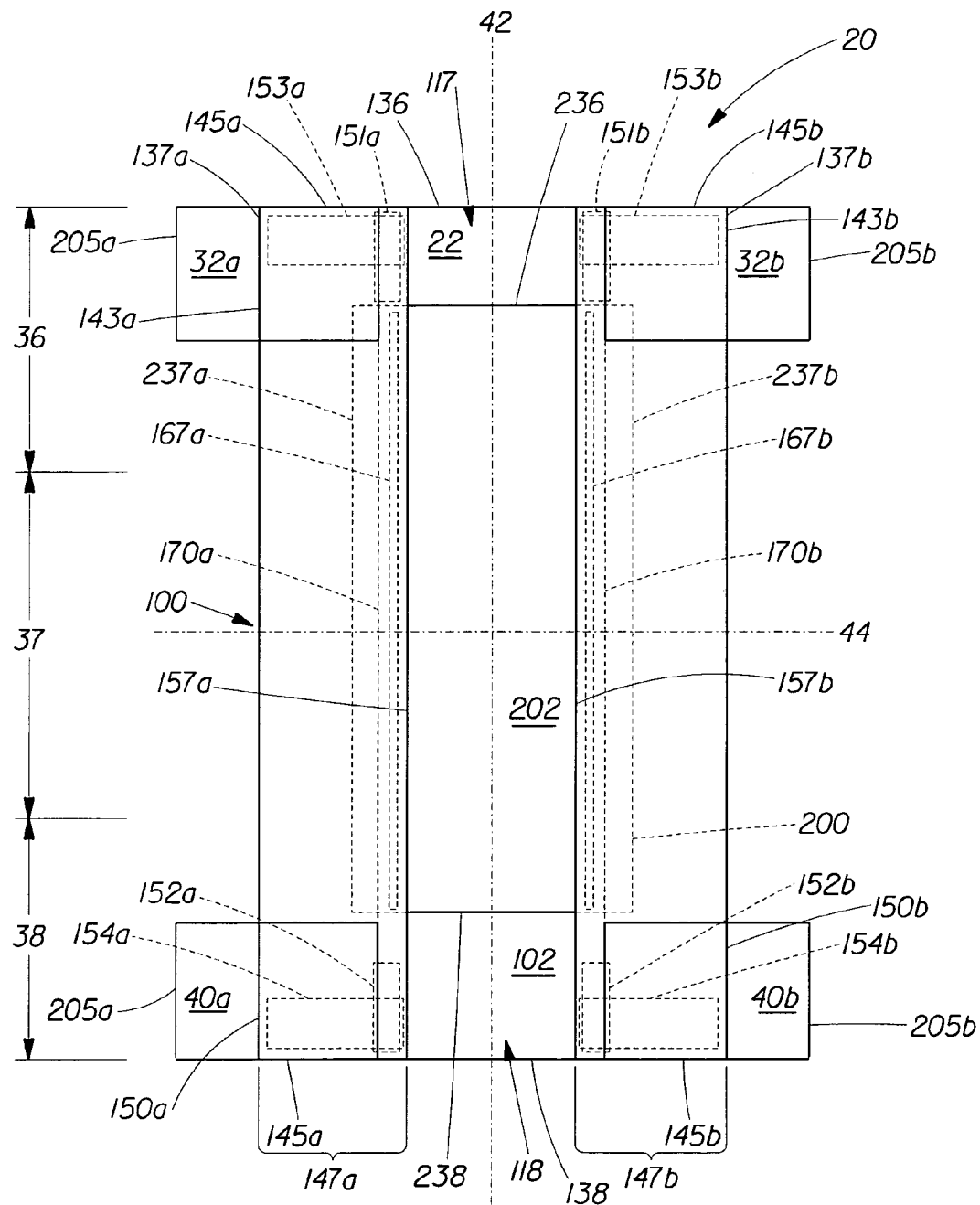
FIG. 19B is a plan view of a pull-on diaper with the diaper shown in its flat, uncontracted state (i.e., without the contraction induced by elastic members), wherein side panels are attached to the chassis to form an "I" configuration constructed in accordance with an alternative embodiment.

Alternatively, referring to FIG. 19B, an "I"-shaped non-rectangular configuration of the chassis 100 can be provided by forming a rectangular chassis 100 as shown in FIG. 1 and attaching an additional element or elements, such as left and right side panels 32 and 40, respectively, to the interior surface of the chassis 100 at or adjacent to each of the side edges 137a and 137b of the chassis 100 to form the respective side panels 32a-b and 40a-b, which can be connected to form a closed diaper 20 of the type described above. It should be appreciated that side panels 32 and 40 can assume any size and shape as desired, and that the side panels 32 and 40 can be attached using any attachment method and apparatus known to those having ordinary skill in the art. Furthermore, the side panels 32 and 40 can extend as longitudinally inward from front and back side edges 136 and 138 as desired. Moreover, side panels 32 and 40 may terminate longitudinally inward from front and back side edges 136 and 138.

Figure 19C:
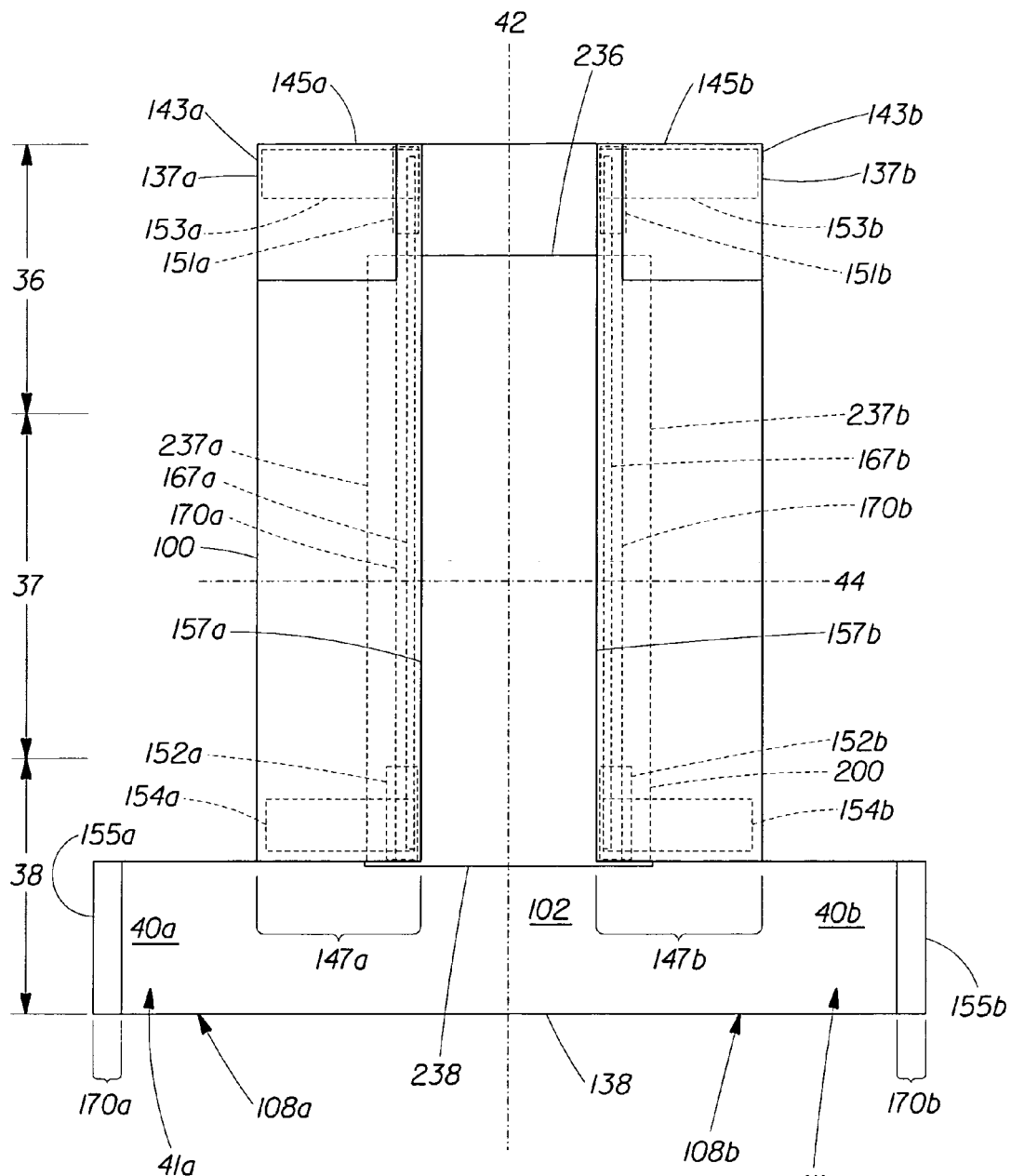
FIG. 19C is plan view of a pull-on diaper constructed in accordance with still another alternative embodiment with the diaper shown in its flat, uncontracted state (i.e., without the contraction induced by elastic members) in which portions of the chassis are left laid out flat when other portions are folded laterally inward to form side flaps in a "T" configuration.

While FIGS. 19A and 19B illustrate the pull-on diaper 20 having the side panels 32 and 40 disposed in both waist regions 36 and 38, FIG. 19C illustrates the diaper 20 being provided with only side panels 40 disposed in the back waist region 38, thereby defining a "T" configuration. The closed side interfaces 119a and b can be formed by attaching the side panel regions 41a and 41b to the corresponding side edge regions 145a and 145b of the chassis 100 in the front waist region 36. Alternatively, the diaper 20 could assume a "T" configuration by providing only side panels 32 in the front waist region. Alternatively still, the diaper 20 could assume a "T" configuration by attaching side panels to the chassis 100 as illustrated and described above with reference to FIG. 19B.

Figure 20:
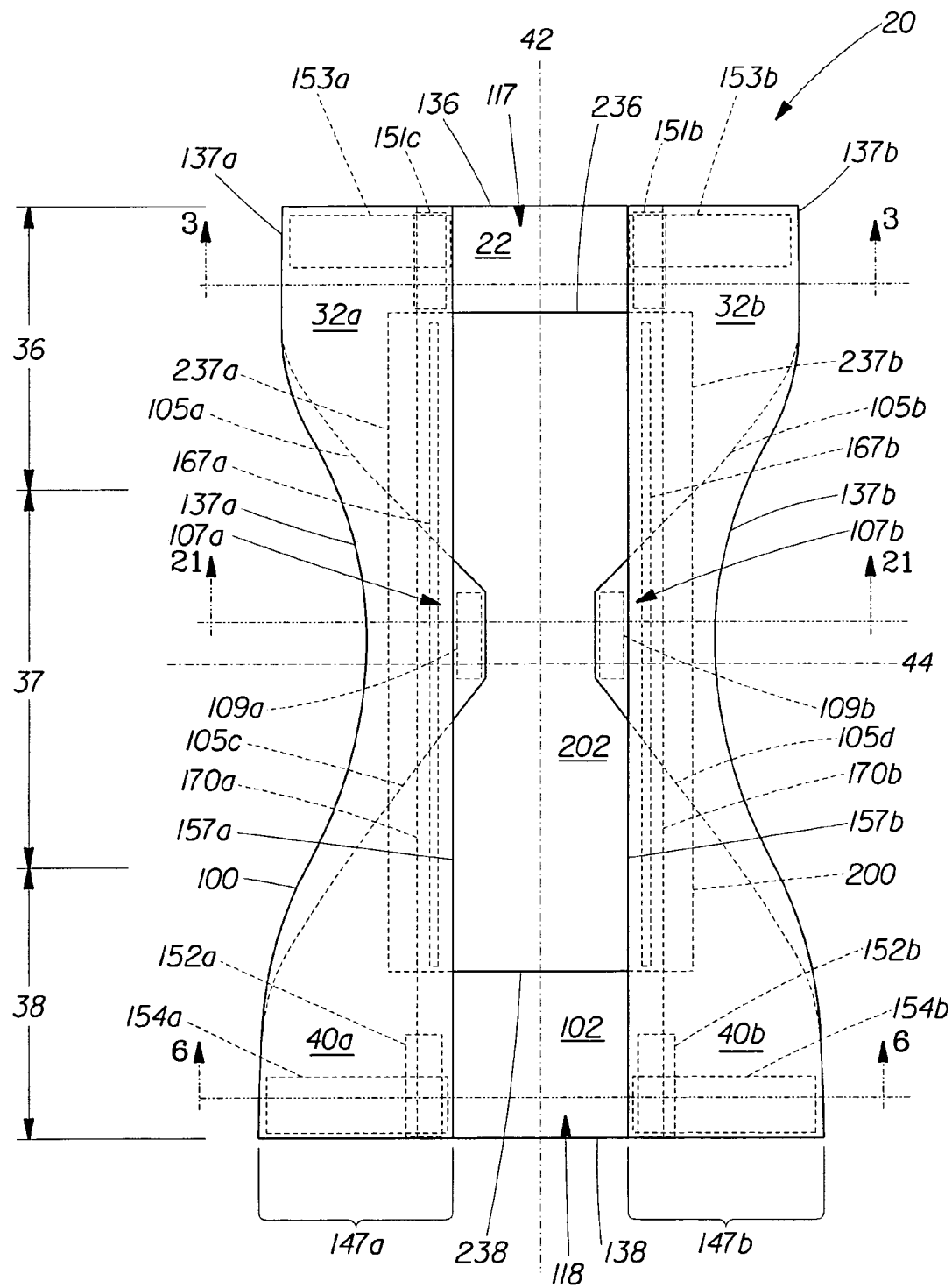
FIG. 20 is a plan view of a pull-on diaper an exemplary diaper constructed in accordance with still another alternative embodiment with the diaper shown in its flat, uncontracted state prior to being configured as a pull-on diaper (i.e., without the contraction induced by elastic members) in which portions of the chassis and side flaps are folded over and attached to the interior surface of the absorbent assembly to impart an hourglass shape to the diaper.
Figure 21:
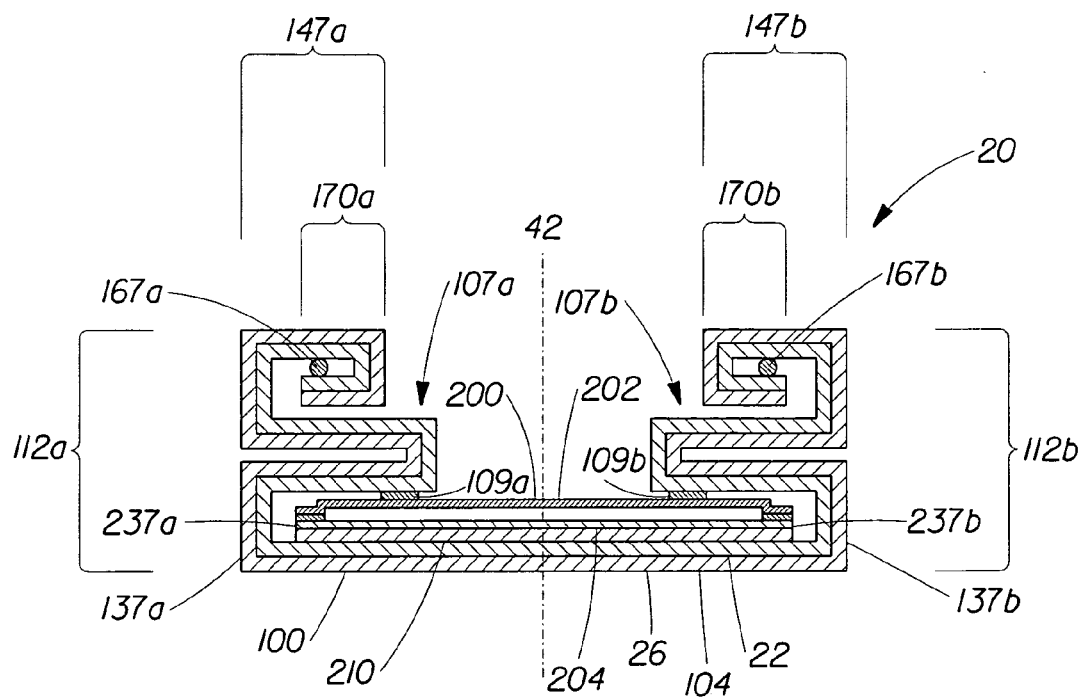
FIG. 21 is a section view of the diaper illustrated in FIG. 20 taken along line 21-21.

Alternatively, referring to FIGS. 20-21, the present invention recognizes that the chassis 100 can assume a non-rectangular configuration, such as an hourglass-shaped configuration. Specifically, laterally opposing portions 107a and 107b of the chassis between each of the side edges 137a and 137b and the respective proximal edges 157a and 157b of the side flaps 147a and 147b can be folded laterally inward in the crotch region 37 along respective diagonal fold lines 105a, 105b, 105c, and 105d such that each of the folded portions 107a and 107b of the chassis overlaps the absorbent assembly 200 in the crotch region 37. The interior surface 102 of each of the folded portions 107a and 107b can be attached to the interior surface 202 of the absorbent assembly in the crotch region 37 at attachment zones 109a and 109b. "W" shaped folds 112a and 112b are thus created in the chassis 100 at the crotch region 37 while retaining the configuration of the waist regions 36 and 38 (shown in FIGS. 3 and 6). The front and back side panels 32a-b and 40a-b are thus defined by those regions of chassis formed disposed proximal the left and right side edges 137a and 137b located above and below the diagonal fold lines 105a, 105b, 105c, and 105d. The attachment zones 109a and 109b can either be disposed symmetrically or asymmetrically with respect to either or both of the longitudinal axis 42 and the lateral axis 44. For example, the attachment zones 109a and 109b shown in FIG. 20 are disposed symmetrically with respect to the longitudinal axis 42 and asymmetrically with respect to the lateral axis 44.

Alternatively, the laterally opposing portions 107a and 107b of the chassis can be folded laterally inward in one or both of the waist regions in addition to being folded laterally inward in the crotch region. For instance, in order to simplify the manufacture of the diaper, the laterally opposing portions 107a and 107b of the chassis 100 can be folded laterally inward over their entire longitudinal lengths. The interior surface 102 of each of the folded portions 107a and 107b can be attached to the interior surface 202 of the absorbent assembly 200 in the crotch region 37 at attachment zones 109a and 109b. This folding and attachment forms "W" shaped folds 112a and 112b in the chassis as shown in FIG. 21 over the entire longitudinal lengths of the laterally opposing portions 107a and 107b of the chassis. An hourglass shape can subsequently be imparted to the chassis 100 when the laterally opposing portions are laterally extended by unfolding at their longitudinally distal ends to prepare the disposable diaper 20 for use in the configuration shown in FIG. 20.

Part or all of the chassis 100 can be made extensible to a degree greater than the inherent extensibility of the material or materials from which the chassis is made (e.g., the backsheet 26, the inner liner 22, or both). Advantageously, the extensible chassis 100 can exhibit an elastic-like behavior in the direction of elongation without the use of added elastic materials. The elastic-like behavior can be modified and/or provided as desired in a web material 325 (FIG. 22) as described below. The additional extensibility may be desirable in order to allow the chassis 100 to conform to the body of a wearer during movement by the wearer. The additional extensibility may also be desirable, for example, to allow the user of a pull-on diaper 20 including a chassis 100 having a particular size before extension to extend the front and/or back waist regions 36 and 38 to enable the pull-on diaper to be pulled over the hips of the wearer and then to contract to encircle the waist of an individual wearer whose waist circumference is typically smaller than the circumference as measured at the hips of the wearer. Such extension of the waist region(s) can give the pull-on diaper 20 a generally hourglass shape, so long as the crotch region 37 is extended to a relatively lesser degree than the waist region(s), and can impart a tailored appearance to the pull-on diaper 20 when it is worn. In addition, the additional extensibility may be desirable in order to minimize the cost of the pull-on diaper 20. Specifically, a lesser amount of material is needed in order to make a diaper capable of being properly fit onto a given size of a wearer when the material is made extensible as described.

Additional extensibility in the chassis 100 in the lateral direction is relatively more useful than additional extensibility in the longitudinal direction. The abdomen of the wearer is likely to expand when the wearer changes posture from standing to sitting and the corresponding abdominal expansion increases the circumference that is encircled by the waist edges of the chassis 100, rendering lateral extension of the waist region or regions particularly advantageous.

Figure 22:
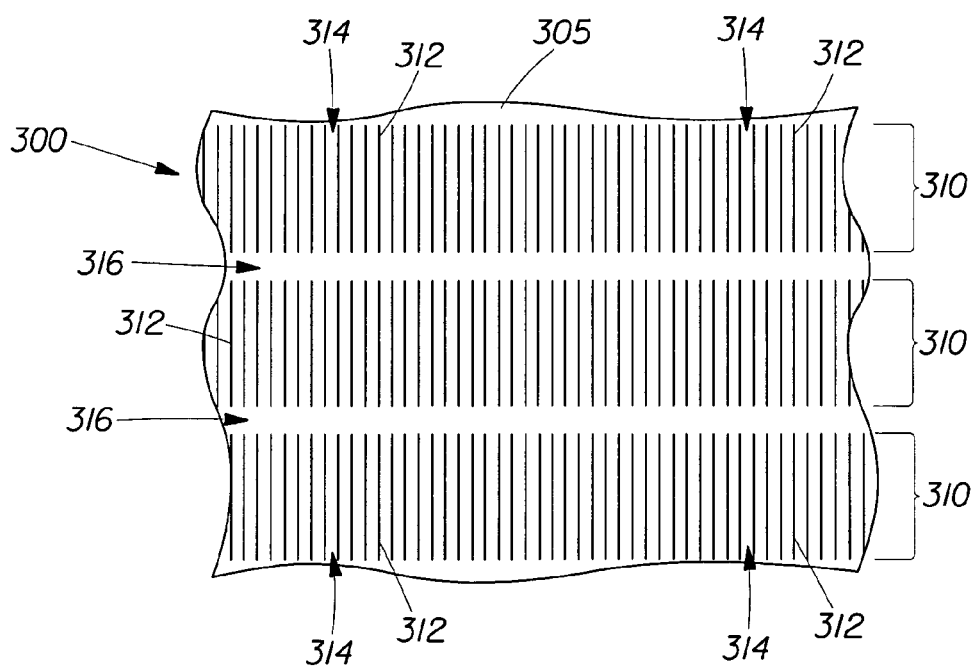
FIG. 22 is a plan view of an exemplary fragment of a formed web material.

Additional lateral extensibility in the chassis 100 can be provided in a variety of ways. For example, a material or materials from which the chassis 100 is made can be pleated by any of many known methods. Alternatively, all or a portion of the chassis 100 can be made of a formed elastic-like web material or a formed laminate of web materials like those described in U.S. Pat. No. 5,518,801 (issued May 21, 1996 to Chappell et al), U.S. Pat. No. 5,691,035 (issued Nov. 25, 1997 to Chappell et al), U.S. Pat. No. 5,723,087 (issued Mar. 3, 1998 to Chappell et al), U.S. Pat. No. 5,891,544 (issued Apr. 6, 1999 to Chappell et al), and U.S. Pat. No. 5,968,029 (issued Jan. 19, 1999 to Chappell et al). An exemplary fragment 320 of such a formed web material 325 is shown in FIG. 22. This formed web material 325 includes distinct laterally extending regions 310 in which the original material has been altered by embossing or another method of deformation to create a pattern of generally longitudinally oriented alternating ridges 312 and valleys 314. The formed web material 325 also includes laterally extending unaltered regions 316 located between the laterally extending altered regions 310.

Such a formed web material 325 can be laterally extended beyond its original dimension with the application of relatively less force than that required to extend the same material to the same extent when undeformed. In particular, the effects of an application of opposing divergent forces directed generally perpendicular to the ridges 312 and valleys 314 include an extension of such a formed web material along an axis between the opposing forces and the generation of a resistive contractive force, primarily in the unaltered regions 316. This resistive force is relatively smaller than the resistive force that is generated by the same material in its unaltered form when extended to the same extent, at least up to an extension at which the ridges and valleys in the altered regions flatten and begin to contribute to the resistive force. Thus, such formed web materials exhibit an extensible behavior resembling that of traditional elastic materials in the range of extensibility that is useful for the type of lateral extension desired for use in absorbent articles. However, such formed web materials can be made of relatively less expensive materials that are not inherently elastic and, thus, their use can provide an advantage in terms of the cost of manufacturing the absorbent articles.

The range of extensibility of a web material or a laminate that is formed as described in the Chappell et al. '801 patent can be controlled by the degree of deformation of the altered regions and can be varied from near zero to a maximum that is dependent upon the original material. For example, the materials used in the chassis 100 (e.g., the backsheet 26) of the exemplary pull-on diaper 20 can typically be formed to provide any range of extensibility from a minimum of 20% to a maximum of more than 100 percent of the original dimension. In some embodiments of the present invention, a portion of the chassis 100 can have a level of extensibility within a range whose lower end is defined by and between 20%, 25%, and 30%, and whose upper end is defined by and between 40%, 60%, and 80%. The requisite levels of extensibility are achieved by application of an opposing divergent force in the direction of extensibility of preferably less than 1,000 grams/inch, more preferably less than 700 grams/inch. However, it should be easily appreciated that any particular value for the maximum extensibility in the range from approximately twenty percent to approximately 100 percent can be selected to suit a particular choice of the original size of the diaper 20 and the range of sizes of the intended wearers. In particular, a diaper having a specific unextended waist opening circumference can be suitable for use on wearers having waist circumferences ranging from equal to this unextended waist opening circumference up to the maximum extensibility.

When the web 325 is subjected to an applied elongation, the web material exhibits an elastic-like behavior as it extends in the direction of applied elongation and returns to its substantially untensioned condition once the applied elongation is removed, unless the web material is extended beyond the point of yielding. The web extensibility is adjustable by varying the percentage of the web surface which is comprised of the ridges 312 and valleys 314. This can be achieved, for instance, by modifying the widths of the ridges 312 and valleys 314, and the spacing between adjacent ridges 312 and valleys 314. A higher percentage of area coverage of the web material 325 by the ridges 312 and valleys will increase the overall extensibility of the web 325. The web 325 is able to undergo multiple cycles of applied elongation up to the yield point without losing its ability to substantially recover. Accordingly, the web 325 is able to return to its substantially untensioned condition once the applied elongation is removed (e.g., as the chassis 100 is pulled over the wearer's waist region during use).

The front laterally central portion 117 and the back laterally central portion 118 of the chassis 100 between the attachment zones 151-154 where the side flaps 147a and 147b are attached to the interior surface 102 of the chassis 100 adjacent to the respective waist edges 137 and 138 can have a different range of extensibility from the portions of the chassis 100 in the attachment zones. Additionally or alternatively, the laterally central portions 117 and 118 can be extensible to a greater or lesser degree when subjected to a given level of opposing tensile forces, and can thus be more easily or less easily extensible than the portions of the chassis in the attachment zones 151-154. For example, if the chassis 100 is made uniformly extensible across its entire width prior to the formation of the side flaps 147a and 147b, the double layering in the areas of the attachment zones after the formation of the side flaps can have an effect of decreasing the degree of lateral extensibility of those areas under a given level of opposing tensile forces, such as by the side flaps acting as parallel "springs" that must be extended in order to extend the underlying attached portion of the chassis. As another example, the altered regions in the laterally central portions of the chassis can be deformed to a greater or a lesser degree than the altered regions in the attachment zones to render the laterally central portions more easily or less easily extensible than the respective portions in the attachment zones. Such differential range of extensibility and/or differential relationship of tensile force to extensibility may be desirable. For example, when the waist regions are laterally extended by a user when applying a pull-on diaper to the body of a wearer, each waist region is typically subjected to a generally uniform level of opposing tensile forces across its entire width, so long as the user grasps the diaper 20 at or adjacent to the laterally opposing side edges 137*a* and 137*b*. If the laterally central portion of the chassis is less easily extensible than the portions in the attachment zones, the lateral spacing between the proximal edges 157*a* and 157*b* of the side flaps 147*a* and 147*b* will increase less under a given level of applied tensile forces than if the laterally central portion were equally easily extensible or more easily extensible than the portions in the attachment zones 143*a-b* and 150*a-b*. This effect of minimizing the change in the lateral spacing between the side flaps 147*a* and 147*b* can help to ensure that the pull-on diaper 20 fits as intended on the body of the wearer by, for example, making it more likely that the proximal edges 157*a* and 157*b* of the side flaps 147*a* and 147*b* will fit into the leg creases of the body while the pull-on diaper 20 is being worn.

Any of a variety of extensible materials can be formed as described in the Chappell et al. '801 patent. For example, a film, a nonwoven, or a laminate of either or both of these materials can be formed to provide the desired extensibility. It is also possible to modify such a material in more than one way while forming it to provide extensibility. For instance, a film that is originally formed to resist the permeation of vapor through its thickness and to contain fine particles of a granular filler material such as calcium carbonate can be treated as described in the Chappell et al. '801 patent to simultaneously provide extensibility and create small holes that allow water vapor to pass through its thickness. Thus, the film can simultaneously be rendered extensible and breathable. Alternatively, a portion of the backsheet 26 can be ring-rolled and thus rendered highly extensible as described in U.S. Pat. No. 5,366,782 (issued Nov. 22, 1994 to Curro, et al). Specifically, a ring-rolling apparatus includes opposing rolls having intermeshing teeth that incrementally stretch and thereby plastically deform the material forming backsheet 26 (or a portion thereof) thereby rendering the backsheet 26 extensible in the ring-rolled regions. In one embodiment, the backsheet 26 can be ring-rolled in a portion of at least one of the front or back waist regions while other regions may comprise a structured elastic-like formed web material. The chassis may be ring-rolled across the entire width in one or both of the waist regions or alternatively may be ring-rolled over only a portion of the chassis width. In yet another embodiment the chassis may be ring-rolled in the portion of the chassis 100 wherein the side flaps 147 overlap and are joined to the chassis 100 in attachment zones 151, 152, 153, and 154.

Furthermore, once the diaper 20 has been positioned on the lower torso region of the wearer, the web 325 enables the diaper 20 to apply a contractive force at the front and back waist regions 36 and 38, respectively, to the wearer's body at a level greater than 100 grams, alternatively greater than 200 grams, and alternatively still greater than 300 grams. It may also be desired that the chassis applies a contractive force at the waist regions 36 and 38 that is less than 2,000 grams, alternatively less than 1,500 grams and alternatively still less than 1,000 grams. As described in the Chappell et al. '801 patent, the resistive force exerted by the web 325 (i.e., the contractive force) in response to an applied elongation can be modified. Specifically, the web can be designed to yield virtually any resistive force which is less than that of the base web material by adjusting the percentage of the web surface which is comprised of the first and second regions. The higher the percent area coverage of the web 325 by the ridges 312 and valleys 314, the lower the resistive force that the web will exert against an applied elongation for a given material composition and cross-sectional area.

Extension versus force and contractive force can be determined by ASTM 882-02 with the following modifications. A sample representative of the extensible material disposed in the waist region should be collected for the test. In the test a 5.08 cm by 15.24 cm (2 inch by 6 inch) sample is cut from the material such that the edges are straight. The sample is clamped into the tensile tester. The clamps are attached 10.16 cm (4 in) from each other on the sample. The sample is pulled steadily at a speed of 2.54 cm/min (1 in/min) to 20% extension and then immediately returned to 0% (4 in. spacing between the clamps) at the same steady speed. Data, extension in mm and force in grams, should be collected at a rate of at least 1 data point per second. The data can be graphed to provide a curve of % extension versus force such that the extension at various tensile/contractive forces can be determined. The extension force can be determined by the extension curve and the contractive force can be determined by the return curve. This test should be repeated at 30, 40, 50, 60, 70, 80, 90 and 100% extension using a new specimen for each test. A representative sampling should be made for each condition.

To compare the extension force and contractive force of one pull-on diaper to another, the diaper in question is applied to a representative group of wearers within the specified size range of the diaper and the circumferential waist dimension of the diaper and/or wearer is determined. The circumferential waist dimension of the diaper as worn is then compared to the diaper waist circumference in a new unextended state. The % extension is derived by the following:

$$(\text{As-worn waist circumference} - \text{original waist circumference})/\text{original waist circumference}$$

Once the percentage waist extension is calculated, a correlating force can be established using the above-described method. It should thus be appreciated that, for a given diaper, a force-% extension relationship can be determined as described above.

Description of the Absorbent Assembly

Figure 23:
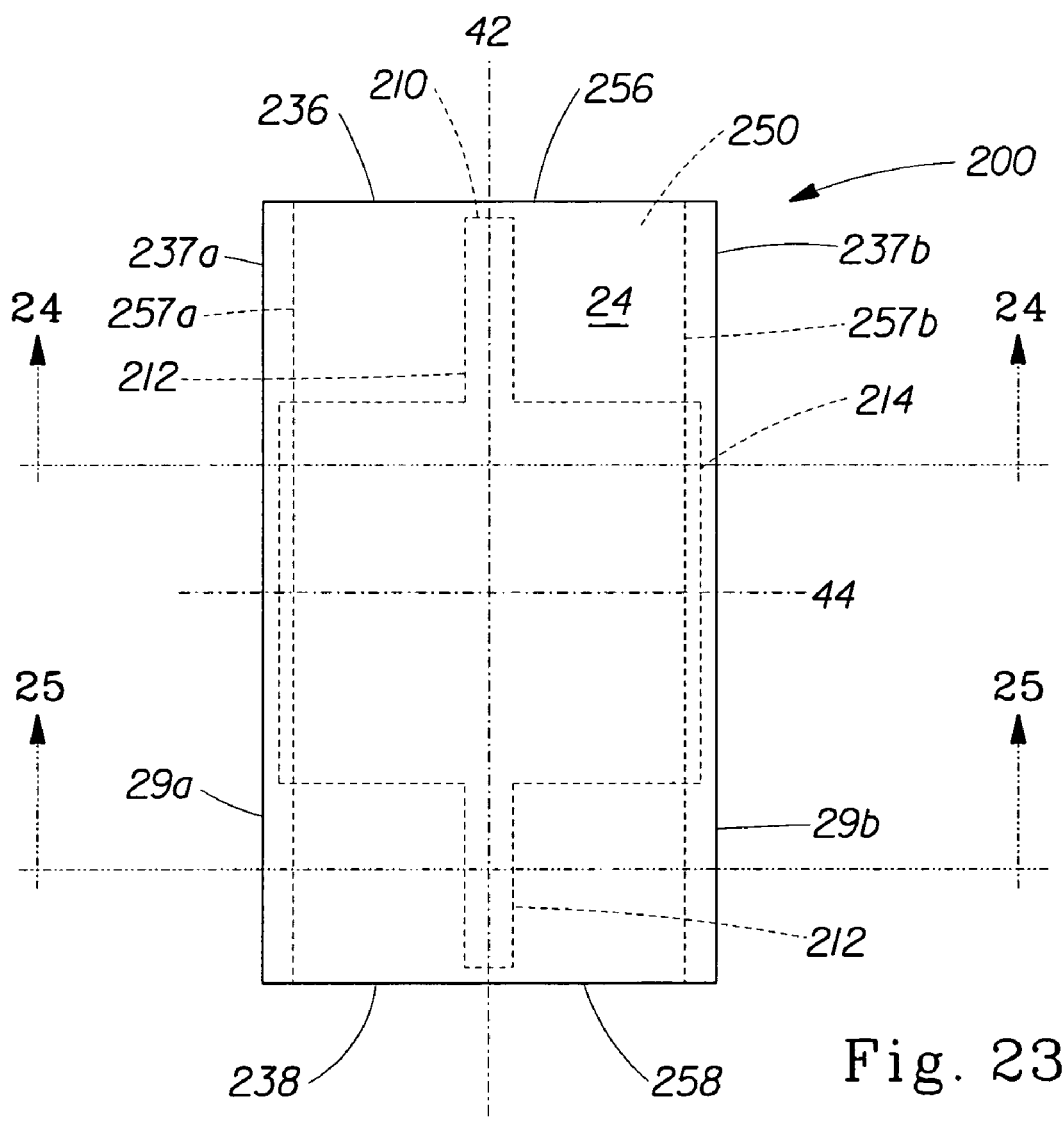
FIG. 23 is a plan view of an absorbent assembly, with the interior portion of the absorbent assembly that faces inwardly toward the wearer and contacts the wearer shown facing the viewer, in which the absorbent assembly is shown separate from a chassis to which it is attached in an exemplary diaper.
Figure 24:
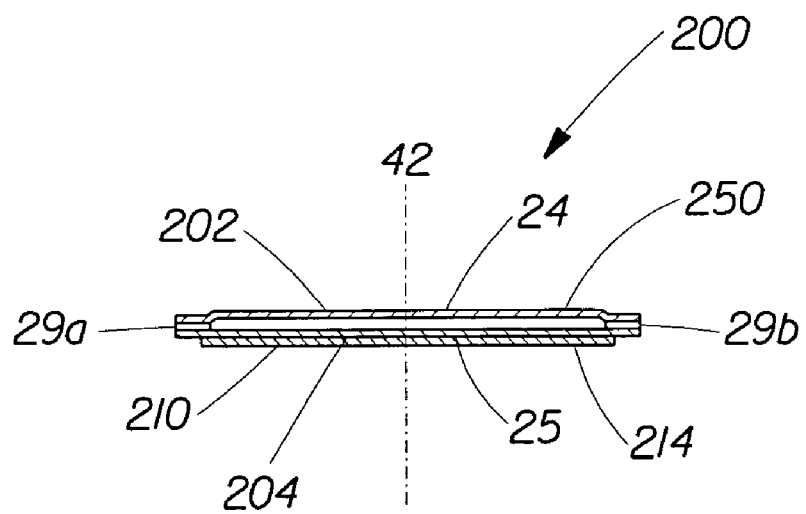
FIG. 24 is a section view of the absorbent assembly illustrated in FIG. 23 taken along line 24-24.
Figure 25:
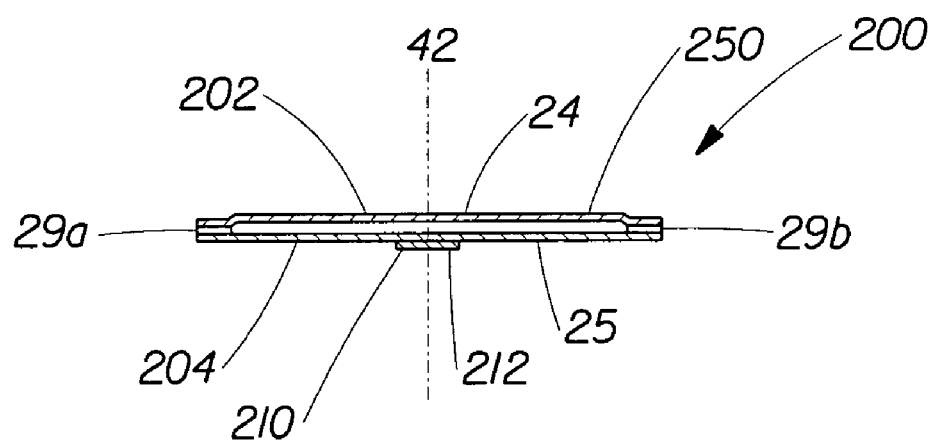
FIG. 25 is a section view of the absorbent assembly illustrated in FIG. 23 taken along line 25-25.

As shown in FIGS. 23-25, the absorbent assembly 200 includes an absorbent core 250. The absorbent core 250 has a laterally extending front edge 256 in the front waist region 36 and a longitudinally opposing and laterally extending back edge 258 in the back waist region 38. The absorbent core 250 also has a longitudinally extending left side edge 257*a* and a laterally opposing and longitudinally extending right side edge 257*b*, both absorbent core side edges extending longitudinally between the front edge 256 and the back edge 258. Any or all of the respective front edge 256, back edge 258, left side edge 257*a*, and right side edge 257*b* of the absorbent core 250 can lie inward of the respective front edge 236, back edge 238, left side edge 237*a*, and right side edge 237*b* of the absorbent assembly 200. For example, in the exemplary absorbent assembly 200 shown in FIG. 23, the absorbent core 250 has its left side edge 257*a* and right side edge 257*b* located laterally inward of, respectively, the left side edge 237*a* and right side edge 237*b* of the absorbent assembly 200. Alternatively, one or more of the edges of the absorbent core 250 can coincide with the corresponding edge of the absorbent assembly 200. For example, in the exemplary absorbent assembly 200 shown in FIG. 23, the front edge 256 and back edge 258 of the absorbent core 250 coincide with the respective front edge 236 and back edge 238 of the absorbent assembly 200.

The absorbent assembly 200 can be attached to the chassis 100 over any part or the whole of the area of the absorbent assembly 200. In one aspect of the present invention, the absorbent assembly 200 is attached on its exterior surface 204 to the chassis 100, and in particular to the backsheet 26, in a cruciform attachment pattern, i.e., in an attachment pattern that forms or is arranged in a cross or "+" shape. The cruciform attachment pattern can be contiguous, i.e., all of its portions can be touching or connected throughout the pattern in an unbroken sequence. Alternatively, the cruciform attachment pattern can include detached portions and thereby lack contiguity but still be arranged such that the shape of the overall pattern is a cruciform. For example, a discontiguous cruciform attachment pattern can include a longitudinally extending portion disposed along the longitudinal axis and separate left and right laterally distal portions disposed along or adjacent to the lateral axis and thereby form a cruciform as the shape of the overall pattern.

An exemplary contiguous cruciform attachment pattern 210 is shown in FIGS. 17 and 23-25. The portions of the chassis 100 that lie outside such a cruciform attachment pattern are not restrained by attachment to the absorbent assembly 200 and therefore remain extensible. In particular, a relatively narrow longitudinally extending portion 212 of a cruciform attachment pattern 210 like that shown in FIGS. 23-25 leaves the majority of the width of the chassis 100 in the front waist region 36 and in the back waist region 38 freely extensible and thereby allows extension of the chassis 100 in the lateral direction in these regions. A relatively wide laterally extending portion 214 of a cruciform attachment pattern 210 like that shown in FIGS. 23-24 prevents the portion of the chassis 100 in the crotch region 37 to which the absorbent assembly 200 is attached from shifting relative to the absorbent assembly 200 in that region. A relatively wide laterally extending portion 214 of a cruciform attachment pattern 210 can also contribute to the effectiveness of the side flaps 147a and 147b when the elastic strands 167a and 167b lift the proximal edges 157a and 157b into contact with the body of the wearer. For example, if the chassis 100 in the crotch region 37 were free to shift laterally inward, i.e., toward the longitudinal axis 42 such that the left side edge 137a and/or the right side edge 137b moved toward the longitudinal axis 42, the side flaps 147a and 147b might easily distort and fail to maintain contact with the body. However, because. the relatively wide laterally extending portion 214 of the cruciform attachment pattern 210 restrains the chassis 100 over a relatively wide portion of the width of the crotch region 37, the side flaps 147a and 147b are better supported at their bases while being lifted by the elastic strands 167a and 167b.

The cruciform attachment pattern 210 in FIGS. 23-25 extends laterally from near the left side edge 237a to near the right side edge 237b of the absorbent assembly 200 at and adjacent to the lateral axis 44, but does not extend laterally to this extent over the full length of the absorbent assembly 200. Similarly, the cruciform attachment pattern 210 in FIGS. 23-25 extends longitudinally from near the front edge 236 to near the back edge 238 of the absorbent assembly 200 at and adjacent to the longitudinal axis 42, but does not extend longitudinally to this extent over the full width of the absorbent assembly 200. Alternatively, the cruciform attachment pattern 210 can extend to any or all of the side edges 237a and 237b and the front edge 236 and the back edge 238 of the absorbent assembly 200. For example, the cruciform attachment pattern 210 can extend laterally from the left side edge 237a to the right side edge 237b of the absorbent assembly 200, but can extend longitudinally only a part of the distance from the front edge 236 to the back edge 238 of the absorbent assembly 200. Within the extent of the cruciform attachment pattern 210, the absorbent assembly 200 can be attached to the chassis 100 continuously or intermittently. For example, a film of an adhesive can be applied continuously over the entire area of the cruciform attachment pattern and then used to continuously attach the absorbent assembly to the chassis. As an alternative example, an adhesive can be applied discontinuously at and inside the boundaries of the cruciform attachment pattern, such as in the form of dots, stripes, beads, spirals, etc., and then used to attach the absorbent assembly to the chassis.

The cruciform attachment pattern 210 can be disposed symmetrically with respect to either or both of the longitudinal axis 42 and the lateral axis 44 of the chassis 100. Alternatively, the cruciform attachment pattern 210 can be disposed asymmetrically with respect to either or both of the longitudinal axis 42 and the lateral axis 44. For example, the cruciform attachment pattern 210 shown in FIG. 23 is disposed symmetrically with respect to the longitudinal axis 42 and asymmetrically with respect to the lateral axis 44. In particular, the cruciform attachment pattern 210 shown in FIG. 23 is disposed asymmetrically toward the front waist region 36. Also, the laterally extending portion 214 of the cruciform attachment pattern 210 can be located distant from the lateral axis 44 and the longitudinally extending portion 212 of the cruciform attachment pattern 210 can similarly be located distant from the longitudinal axis 42. In addition, the cruciform attachment pattern 210 can be disposed symmetrically with respect to either or both of the side edges 237a and 237b and the front edge 236 and the back edge 238 of the absorbent assembly 200. For example, the cruciform attachment pattern 210 shown in FIG. 23 is disposed symmetrically with respect to both the side edges 237a and 237b and the front edge 236 and the back edge 238, i.e., the cruciform attachment pattern 210 shown in FIG. 23 is centered on the absorbent assembly 200. Alternatively, the cruciform attachment pattern 210 can be disposed asymmetrically with respect to either or both of the side edges 237a and 237b and front edge 236 and back edge 238 of the absorbent assembly 200, i.e., the cruciform attachment pattern 210 can be disposed off-center on the absorbent assembly 200.

It should be appreciated that the portion of the chassis 100 that is attached to the absorbent assembly 200 is not extensible. Advantageously, the cruciform attachment pattern 210 enables attachment of the absorbent assembly 200 to the chassis 100 while, at the same time, providing a significant portion of the chassis 100 that overlaps the absorbent assembly 200 to be free from the chassis 100, particularly in areas in the front waist region 36 and the back waist region 38. Accordingly, the cruciform attachment pattern 210 enables the chassis 100 to be more extensible than an absorbent article whose chassis is connected substantially to a surface of the absorbent assembly or about the periphery of the absorbent assembly. The increased chassis extensibility is useful when, for instance, donning the diaper 20 on the wearer.

Figure 30:
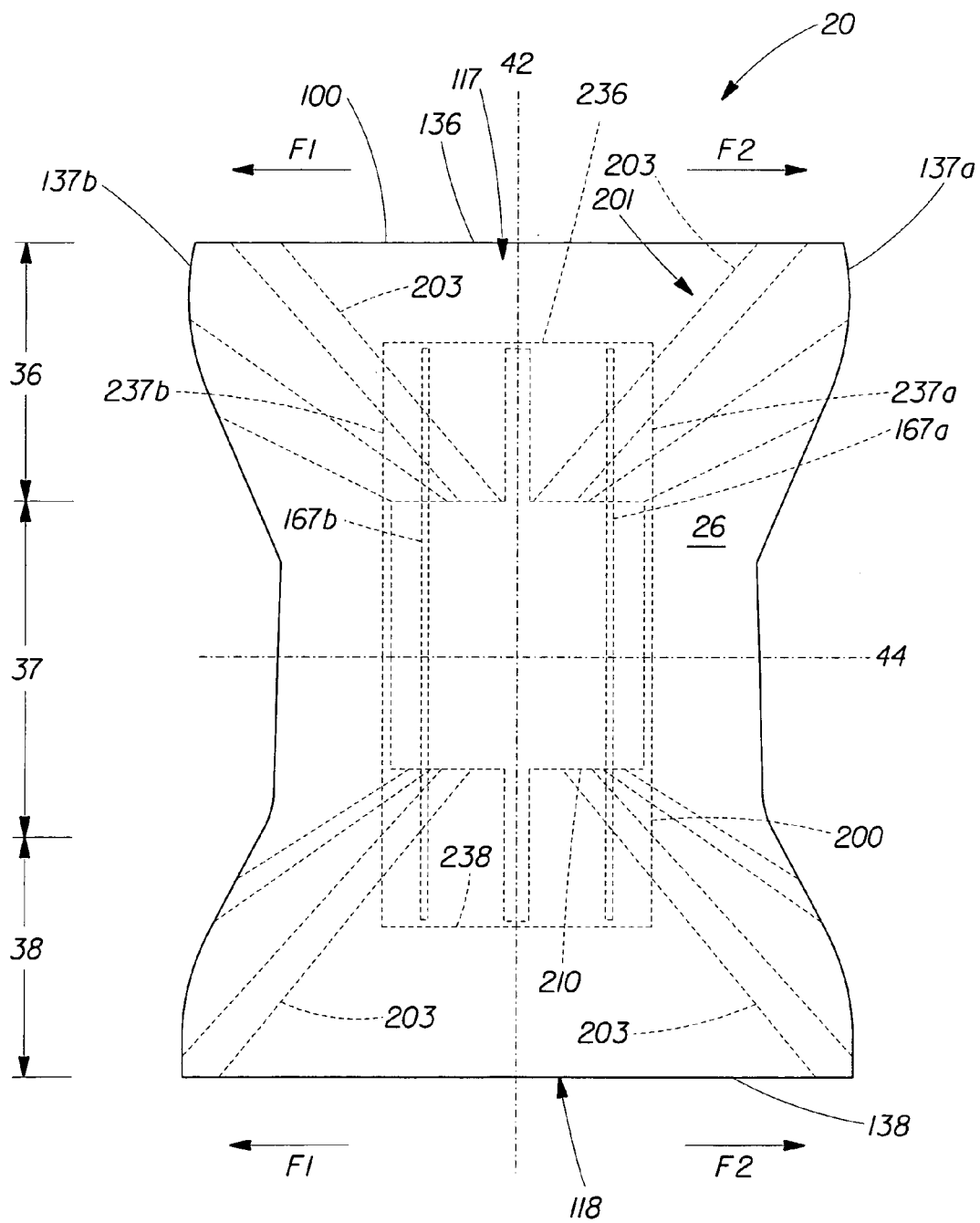
FIG. 30 is a plan view of an exemplary diaper having portions removed to illustrate the diaper in a stretched configuration.

Referring now to FIGS. 22 and 30, the backsheet 26, by virtue of the ridges 312 and valleys 314 described above, is extensible at regions that are free from the absorbent assembly 200, including regions that are disposed directly beneath the absorbent assembly 200 and free from the absorbent assembly 200. The extensibility of portions of the backsheet 26 increases as the portions become increasingly distant from the laterally extending portion 214 of the cruciform pattern 210.

When the pull-on diaper 20 is pulled onto the body of the wearer, a force will be applied by the diaper 20 to the waist region of the user to secure the diaper 20 onto the body of the wearer. Forces applied to the diaper 20 during application are simulated in FIG. 30 as opposing laterally outward forces F1 and F2 applied to the left and right side edges 137a and 137b, respectively, in the front waist region 36 and back waist region 38. Upon application of forces F1 and F2, the backsheet 26 deforms to a significantly greater degree in the waist region than in the crotch region thereby creating angled lines of tension 203 directed from portion 214 of the cruciform pattern 210 to the side edges 137a and 137b in both the front and back waist regions 36 and 38. These angled lines of tension 203 provide an internal support structure 201 integral with the chassis 100 (in particular the backsheet 26), that receives forces from the absorbent assembly 200 and transmits the forces toward the waist regions of the pull-on diaper, specifically toward the closed side interfaces.

The absorbent core 250 can be disposed between a lower covering sheet that is disposed on the exterior face of the absorbent core 250 in a face-to-face arrangement with the interior surface 102 of the chassis and an upper covering sheet that is disposed on the interior face of the absorbent core 250. Such an upper covering sheet and lower covering sheet can be attached together to contain the absorbent core 250 between them and thereby form the absorbent assembly 200. For example, in the exemplary absorbent assembly 200 shown in FIGS. 23-25, an upper covering sheet 24 and a lower covering sheet 25 are attached together at or adjacent to the side edges 237a and 237b of the absorbent assembly 200 in longitudinally extending adhesive attachment zones 29a and 29b. Alternatively, the upper covering sheet 24 and the lower covering sheet 25 can be attached together in places other than the side edges 237a and 237b of the absorbent assembly 200, e.g., at or adjacent to the end edges 236 and 238 of the absorbent assembly 200, or at or adjacent to both the end edges 236 and 238 and the side edges 237a and 237b.

The upper covering sheet 24 is water-permeable and allows liquid waste to pass through to the absorbent core 250, where the liquid waste is absorbed. The lower covering sheet 25 can be water-impermeable. However, the lower covering sheet 25 preferably is water-permeable. In embodiments in which both the upper covering sheet 24 and the lower covering sheet 25 are water-permeable, any liquid waste that is deposited onto the upper covering sheet 24 but does not pass through the upper covering sheet 24 to the absorbent core 250 can flow around an edge of the absorbent assembly 200 to reach the lower covering sheet 25 and then pass through the lower covering sheet 25 to the absorbent core 250.

The upper covering sheet 24 can form the interior surface 202 of the absorbent assembly 200 that is intended to be placed against the body of the wearer. The upper covering sheet 24 preferably is formed of a soft material that will not irritate the skin of the wearer. Many materials that are suitable for a water-permeable covering sheet are well-known in the art, including synthetic nonwovens such as spunbonded or carded polypropylene, polyester, or rayon. Likewise, many materials that are suitable for a covering sheet that is water-impermeable are well-known in the art, including the materials that are suitable for the backsheet 26.

The upper covering sheet 24 and the lower covering sheet 25 can extend to the same width and the same length. Alternatively, one or more of the edges of one of the covering sheets can lie distally relative to the respective edge or edges of the other covering sheet. For example, the upper covering sheet can extend longitudinally only to an extent sufficient to cover the absorbent core and the lower covering sheet can extend longitudinally beyond the upper covering sheet toward or to the adjacent waist edge. Such an extended covering sheet can serve to isolate the skin of the wearer from a portion of the backsheet 26 as may be desirable, for example, when the diaper 20 is worn under conditions in which contact between the skin and a backsheet film could be uncomfortable.

Suitable absorbent materials for the absorbent core 250 are well-known and can comprise any absorbent material that is generally compressible, conformable, non-irritating to the wearer's skin, and capable of absorbing and retaining liquids such as urine and other certain body exudates. The absorbent core 250 may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. The absorbent core 250 can further comprise minor amounts (typically less than 10%) of non-liquid absorbent materials, such as adhesives, waxes, oils and the like. Exemplary absorbent structures for use as the absorbent assemblies are described in U.S. Pat. No. 4,610,678 (Weisman et al.); U.S. Pat. No. 4,834,735 (Alemany et al.); U.S. Pat. No. 4,888,231 (Angstadt); U.S. Pat. No. 5,260,345 (DesMarais et al.); U.S. Pat. No. 5,387,209 (Dyer et al.); U.S. Pat. No. 5,397,316 (LaVon et al.); U.S. Pat. No. 5,625,222 (DesMarais et al.). These absorbent materials can be used separately or in combination. Many known absorbent materials can be used in a discrete form, i.e., in the form of fibers, granules, particles, and the like. Such a discrete form of an absorbent material can be immobilized by an adhesive that attaches the discrete pieces together to form a coherent layer or that attaches the discrete pieces to a substrate layer, such as a covering sheet, or that attaches the discrete pieces both to each other and to the substrate layer. Alternatively, the core 250 can comprise an absorbent polymer material in contact with a thermoplastic material. The absorbent polymer material can be further mixed with an absorbent fibrous material, such as airfelt material, or absorbent core 250 can be substantially airfelt free, as described in U.S. patent application Ser. No. 10/776,851 (Becker et al), published as U.S. Publication. No. 2004/0162536.

Figure 26:
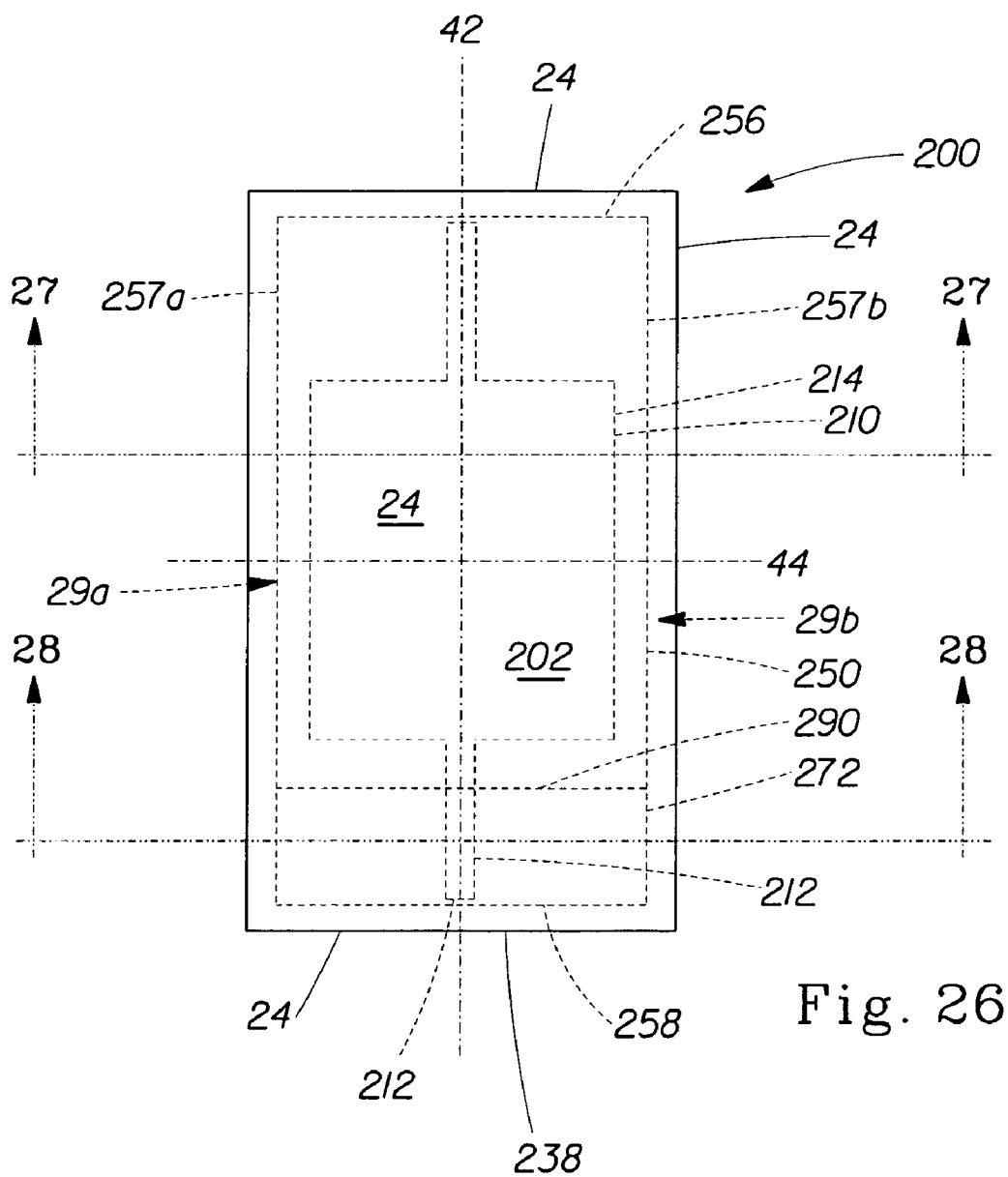
FIG. 26 is a plan view of an absorbent assembly, shown separately from the other portions of an exemplary diaper and with its interior portion facing the viewer.
Figure 27:
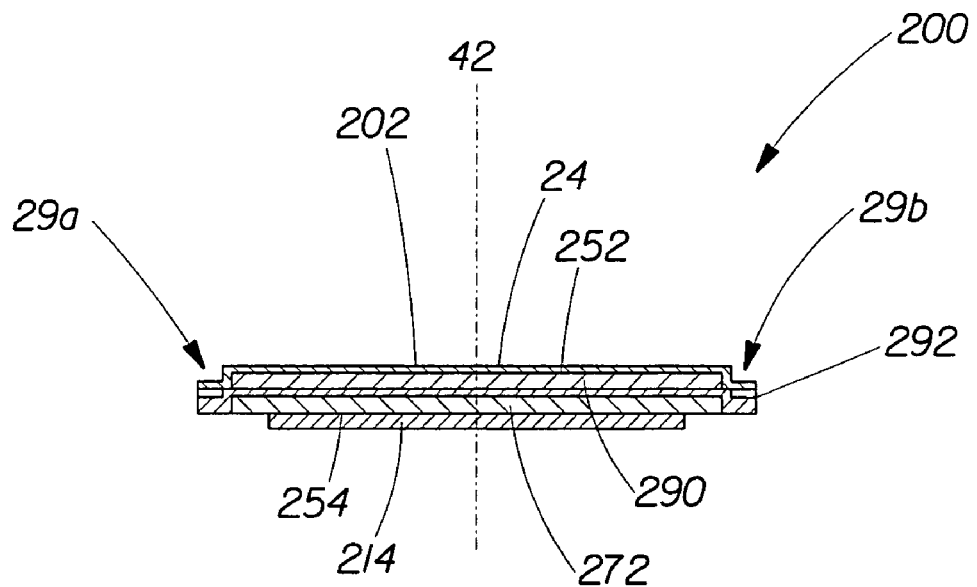
FIG. 27 is a section view of the absorbent assembly of FIG. 26 taken along line 27-27.
Figure 28:
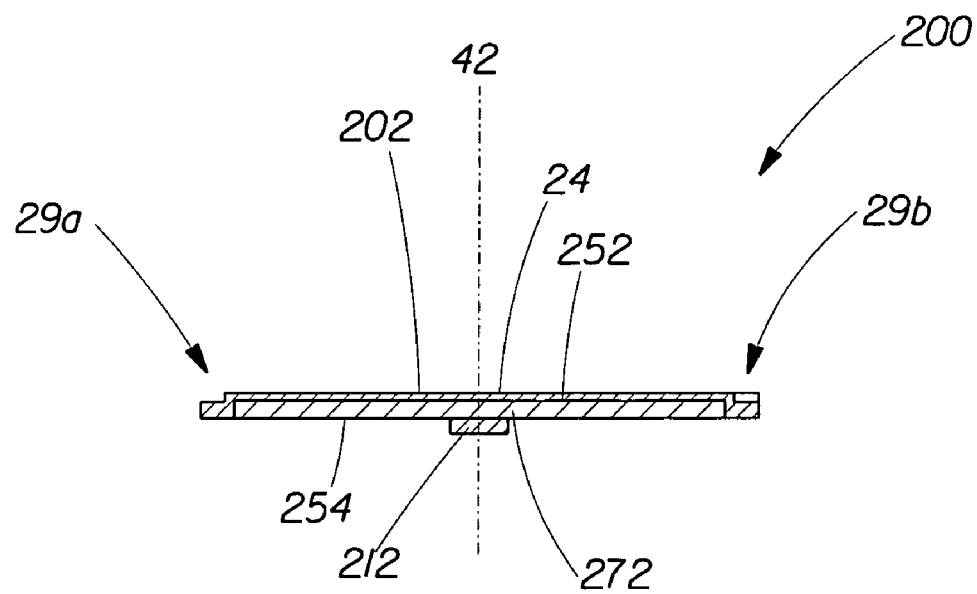
FIG. 28 is a section view of the absorbent assembly of FIG. 26 taken along line 28-28.

Referring to FIGS. 26-28, the absorbent core 250 may include an acquisition component 290 in addition to one or more storage components 272. The absorbent core acquisition component 290 serves to acquire deposited liquid bodily waste material and transfer it to the absorbent core storage component 272. Any porous absorbent material which will imbibe and partition liquid bodily waste material to the storage component or components 272 may be used to form the acquisition component 290. Preferred materials for the acquisition component 290 include synthetic fiber materials, open celled polymeric foam materials, fibrous nonwoven materials, cellulosic nonwoven materials, and various combination synthetic/cellulosic nonwoven materials. For example, the acquisition component may be formed of a nonwoven web or webs of synthetic fibers including polyester, polypropylene, and/or polyethylene, natural fibers including cotton and/or cellulose, blends of such fibers, or any equivalent materials or combinations of materials. Examples of such acquisition materials are more fully described in U.S. Pat. No. 4,950,264 issued to Osborn on Aug. 21, 1990. High loft nonwoven acquisition materials suitable for the acquisition component of the present invention can be obtained from Polymer Group, Inc., (PGI), 450 N.E. Blvd, Landisville, N.J. 08326, U.S.A., under the material code designation of 98920.

Such an absorbent core acquisition component 290 is shown overlying the absorbent core storage component 272 in FIGS. 26-28. A separation sheet 292 of, e.g., a tissue or a nonwoven material, may be disposed between the absorbent core storage component 272 and the absorbent core acquisition component 290 to help ensure that none of the gel formed by a superabsorbent polymer reaches the skin of the wearer. This separation sheet 292 may extend laterally beyond the side edges 257a and 257b of the absorbent core 250 and the upper covering sheet 24 may be attached to the separation sheet 292. In this arrangement, the liquid bodily waste material that is deposited onto the upper covering sheet 24 will pass through the thickness of the upper covering sheet 24 to be absorbed by the absorbent core acquisition component 290, and some or all of it may then pass through the thickness of the separation sheet 292 and then be absorbed and retained by the absorbent core storage component 272.

Figure 29:
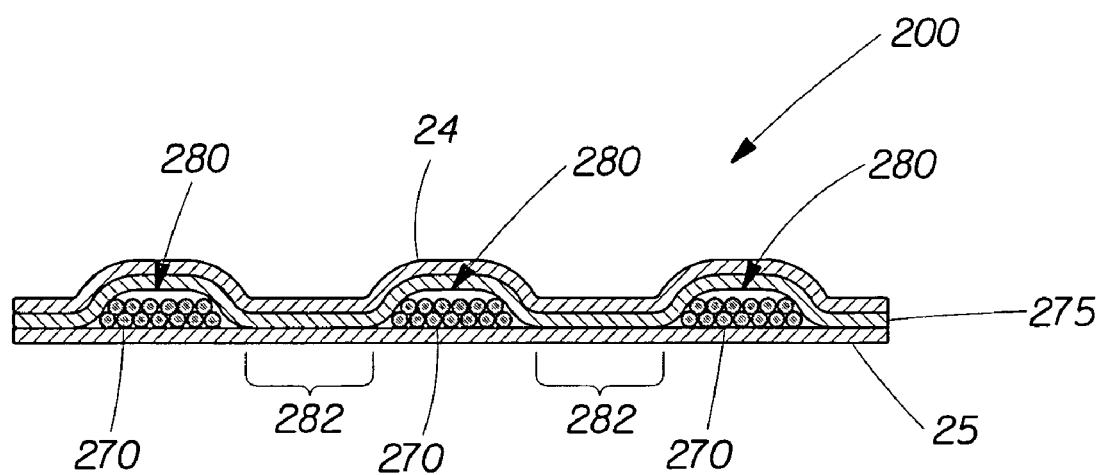
FIG. 29 is a section view of an exemplary absorbent assembly showing details of an absorbent core.

Alternatively, the discrete form of an absorbent material can be immobilized in pockets formed by a layer of a thermoplastic material, such as a hot melt adhesive, that intermittently contacts and adheres to a substrate, such as a covering sheet, while diverging away from the substrate at the pockets. Absorbent assemblies having such structures are described in co-pending and commonly assigned European Patent Applications Nos. 03 002 678.5 and 03 002 677.7, both filed on 12 Feb. 2003 in the name of Ehrnsperger et al. An exemplary absorbent assembly 200 having such a structure is shown in FIG. 29. In this absorbent assembly 200, the absorbent core 250 includes particles of superabsorbent polymer 270 that are contained inside pockets 280 formed by a layer 275 of a thermoplastic material. This absorbent core 250 contains no cellulose fibers. Alternatively, the absorbent core 250 can include both particles of superabsorbent polymer and airfelt and both materials can be contained inside the pockets formed by the layer of the thermoplastic material. As shown in FIG. 29, the layer 275 of the thermoplastic material intermittently contacts and adheres to the lower covering sheet 25 at the areas of attachment 282. Between the areas of attachment 282, the layer 275 diverges away from the lower covering sheet 25 to form the pockets 280. The layer 275 can have the form of a sheet of fibers of the thermoplastic material through which the liquid waste can pass to the particles of superabsorbent polymer 270 to be absorbed.

In FIG. 29, a separate upper covering sheet 24 is shown overlying the layer 275 of the thermoplastic material. Alternatively, the separate upper covering sheet 24 can be omitted and the layer 275 in the form of a fibrous sheet can serve as the upper covering sheet 24. As another alternative, two absorbent assemblies each like that shown in FIG. 29 except for the omission of the upper covering sheet 24 can be superposed with one absorbent assembly inverted such that its pockets nest into the recesses at the areas of attachment 282 of the other absorbent assembly and the respective single covering sheets distally oppose each other. In such a combined absorbent assembly 200, the distally opposing single covering sheets can serve respectively as the upper covering sheet 24 and the lower covering sheet 25.

In the exemplary absorbent assembly 200 shown in FIGS. 23-25, the upper covering sheet 24 and the lower covering sheet 25 are of the same size, i.e., both the upper covering sheet 24 and the lower covering sheet 25 extend to the front edge 236 and back edge 238, as well as to the left side edge 237a and right side edge 237b of the absorbent assembly 200. Alternatively, the upper covering sheet 24 and the lower covering sheet 25 can differ in size. For example, the lower covering sheet 25 can be larger than the upper covering sheet 24 and can be wrapped over the side edges 257a and 257b of the absorbent core 250 onto the interior surface of the absorbent core 250, where the upper covering sheet 24 and the lower covering sheet 25 can be attached together. Alternatively, in place of a separate upper covering sheet 24 and a separate lower covering sheet 25, a single covering sheet can be wrapped around the absorbent core 250 and attached to itself to contain the absorbent core 250. Such a single covering sheet forms an upper layer and a lower layer when wrapped around the absorbent core 250 and, in general, the description of the separate upper covering sheet 24 and lower covering sheet 25 are intended to apply to such upper and lower layers of a wrapped single covering sheet.

At a minimum, the absorbent core 250 is contained laterally by the covering sheet or sheets being wrapped around the absorbent core 250 or attached together at or adjacent to the left side edge 237a and right side edge 237b of the absorbent assembly 200. For example, in the exemplary absorbent assembly 200 shown in FIGS. 23-25, the upper covering sheet 24 and the lower covering sheet 25 are attached together only in left adhesive attachment zone 29a and right adhesive attachment zone 29b at or adjacent to the respective left side edge 237a and right side edge 237b of the absorbent assembly 200. In this embodiment, the upper covering sheet 24 and the lower covering sheet 25 cannot be attached directly together at or adjacent to the front edge 236 and back edge 238 because the absorbent core 250 extends the full length of the absorbent assembly 200, i.e. the front edge 256 and back edge 258 of the absorbent core 250 coincide with the respective front edge 236 and back edge 238 of the absorbent assembly 200. In such an embodiment, the upper and lower layers of the covering sheet or sheets can each be attached to the absorbent core 250 at or adjacent to the front edge 256 and back edge 258 of the absorbent core 250 to form a sandwich. In addition, a sealing agent can be applied at or adjacent to the front edge 256 and back edge 258 of the absorbent core 250 to contain any fibers or particles that might otherwise escape the absorbent core 250. Alternatively, instead of being contained only laterally by the covering sheet or sheets, the absorbent core 250 can additionally be contained longitudinally by the upper and lower layers of the covering sheet or sheets being attached together at or adjacent to the front edge 236 and back edge 238 of the absorbent assembly 200.

All documents cited in the Detailed Description of the Invention are, in relevant part, incorporated herein by reference, however the citation of any document is not construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A disposable absorbent article comprising:
    a front waist region, a back waist region, a crotch region between the waist regions, a front waist side edge, a back waist side edge, a front waist end edge, and a back waist end edge;
    a longitudinal axis extending from a midpoint of the front waist edge through the crotch region to a midpoint of the longitudinally opposed back waist edge;

a web comprising an interior surface and an exterior surface;

an absorbent assembly comprising an interior surface and an exterior surface;

wherein the web is folded over at a first fold line and attached to itself forming a first hem;

wherein the web is folded over at a second fold line and attached to itself forming a second hem;

wherein the web is folded over at a third fold line and attached in the front and back waist regions forming a first side flap, the third fold line forming a first side edge of the absorbent article;

wherein the web is folded over at a fourth fold line and attached in the front and back waist regions forming a second side flap, the fourth fold line forming a second side edge of the absorbent article;

wherein the first side flap comprises the first hem and wherein the second side flap comprises the second hem;

wherein each of the first and second hems comprise a longitudinally extending gathering member;

wherein the first fold line forms a proximal edge of the first side flap and the second fold line forms a proximal edge of the second side flap;

wherein the first and second proximal edges are disposed laterally inward of the first and second side edges;

wherein the first and second proximal edges of the first and second side flaps are disposed between the longitudinal centerline and the first and second side edges, respectively;

a closure member disposed in at least one of the front and back waist regions; and wherein the closure member maintains waist and leg openings of the absorbent article in a closed configuration to form a pant.

2. The disposable absorbent article as recited in claim 1, wherein the side flaps are attached to at least one of the interior surface of the web and the interior surface of the absorbent assembly.

3. The disposable absorbent article as recited in claim 1, wherein the side flaps are attached adjacent the longitunally opposing waist end edges.

4. The disposable absorbent article as recited in claim 1, wherein the closure member is a refastenable closure member.

5. The disposable absorbent article as recited in claim 1, wherein the closure member is a permanent closure member.

6. The disposable absorbent article as recited in claim 1, wherein a seam is formed by attaching a portion of the first side flap disposed in one of the front or back waist regions to a portion of the backsheet disposed in the longitudinally opposing front or back waist regions, respectively.

7. The disposable absorbent article as recited in claim 1, wherein a seam is formed by attaching a portion of the first side flap disposed in the front waist region to a portion of the first side flap disposed in the back waist region.

8. The disposable absorbent article as recited in claim 7, wherein a seam is formed by attaching a portion of the second side flap disposed in the front waist region to a portion of the second side flap disposed in the back waist region.

9. The disposable absorbent article as recited in claim 1, wherein a seam is formed by attaching a portion of the backsheet disposed in the front waist region to a portion of the backsheet disposed in the back waist region.

10. The disposable absorbent article as recited in claim 1, wherein at least a portion of the web in one of the waist regions is laterally extensible to a maximum extensibility greater than a maximum extensibility of at least a portion of the web in the crotch region.

11. The disposable absorbent article as recited in claim 1, wherein the absorbent assembly comprises a first and second covering sheet and an absorbent core, and wherein the first covering sheet is disposed on an interior face of the absorbent core and the second covering sheet is disposed on an exterior face of the absorbent core.

12. The disposable absorbent article as recited in claim 1, wherein the waist opening is configured to apply a contractive force within the range of 100 grams to 2000 grams.

13. The disposable absorbent article as recited in claim 1, wherein the waist opening is configured to apply a contractive force within the range of 300 grams to 1000 grams.

14. The disposable absorbent article as recited in claim 1, wherein the absorbent assembly is attached to the backsheet via an attachment pattern comprising a longitudinally extending portion disposed along the longitudinal axis and at least one discontiguous laterally distal portion.

\* \* \* \* \*